(12) United States Patent
Mitsukami et al.

(10) Patent No.: US 7,745,507 B2
(45) Date of Patent: *Jun. 29, 2010

(54) ABSORBENT MEMBER COMPRISING A MODIFIED WATER ABSORBENT RESIN

(75) Inventors: Yoshiro Mitsukami, Himeji (JP); Makoto Matsumoto, Himeji (JP); Taku Iwamura, Himeji (JP)

(73) Assignee: The Procter & Gamble Company, Cincinnati, OH (US)

( * ) Notice: Subject to any disclaimer, the term of this patent is extended or adjusted under 35 U.S.C. 154(b) by 255 days.

This patent is subject to a terminal disclaimer.

(21) Appl. No.: 11/732,589

(22) Filed: Apr. 4, 2007

(65) Prior Publication Data
US 2007/0238806 A1 Oct. 11, 2007

(30) Foreign Application Priority Data

| Apr. 10, 2006 | (JP) | 2006-108083 |
| Jun. 6, 2006 | (JP) | 2006-157582 |

(51) Int. Cl.
C08J 3/28 (2006.01)
C08J 7/18 (2006.01)
C08K 3/30 (2006.01)
C08K 5/14 (2006.01)

(52) U.S. Cl. ............... 522/49; 522/60; 522/61; 522/62; 522/84; 522/86

(58) Field of Classification Search ............ 522/84, 522/85, 49, 86, 60, 61, 62
See application file for complete search history.

(56) References Cited

U.S. PATENT DOCUMENTS

| 3,214,492 A | 10/1965 | Tocker |
| 3,429,852 A | 2/1969 | Martin |
| 3,622,848 A | 11/1971 | Hendrix, et al. |
| 3,661,875 A | 5/1972 | Sieja |
| 3,860,003 A | 1/1975 | Buell |
| 3,935,099 A | 1/1976 | Weaver et al. |
| 3,959,569 A | 5/1976 | Burkholder, Jr. et al. |
| 4,043,887 A | 8/1977 | Pacifici et al. |
| 4,062,817 A | 12/1977 | Westerman |
| 4,076,663 A | 2/1978 | Masuda et al. |
| 4,093,776 A | 6/1978 | Aoki et al. |
| 4,124,748 A | 11/1978 | Fujimoto et al. |
| 4,286,082 A | 8/1981 | Tsubakimoto et al. |
| 4,304,895 A | 12/1981 | Loshaek |
| 4,367,323 A | 1/1983 | Kitamura et al. |
| 4,389,513 A | 6/1983 | Miyazaki |
| 4,446,261 A | 5/1984 | Yamasaki et al. |
| 4,514,345 A | 4/1985 | Johnson et al. |
| 4,610,678 A | 9/1986 | Weisman et al. |
| 4,625,001 A | 11/1986 | Tsubakimoto et al. |
| 4,654,039 A | 3/1987 | Brandt et al. |
| 4,666,983 A | 5/1987 | Tsubakimoto et al. |
| 4,683,274 A | 7/1987 | Nakamura et al. |
| 4,690,996 A | 9/1987 | Shih et al. |
| 4,721,647 A | 1/1988 | Nakanishi et al. |
| 4,734,478 A | 3/1988 | Tsubakimoto et al. |
| 4,738,867 A | 4/1988 | Itoh et al. |
| 4,748,076 A | 5/1988 | Saotome |
| 4,769,427 A | 9/1988 | Nowakowsky et al. |
| 4,783,510 A | 11/1988 | Saotome |
| 4,834,735 A | 5/1989 | Alemany et al. |
| 4,847,137 A | 7/1989 | Kellen et al. |
| 4,873,299 A | 10/1989 | Nowakowsky et al. |
| 4,910,250 A | 3/1990 | Saotome |
| 4,922,004 A | 5/1990 | Kohler et al. |
| 4,940,464 A | 7/1990 | Van Gompel et al. |

(Continued)

FOREIGN PATENT DOCUMENTS

| DE | 19 619 680 A | 11/1997 |
| DE | 10 221 202 A | 7/2003 |
| EP | 0 248 437 A2 | 12/1987 |
| EP | 0 279 475 A2 | 8/1988 |
| EP | 0 246 848 A | 11/1988 |
| EP | 0 377 191 A2 | 7/1990 |
| EP | 0 514 775 A1 | 11/1992 |
| EP | 0 287 970 B1 | 1/1994 |

(Continued)

OTHER PUBLICATIONS

J. Phys. Chem. 1975, 79, 2693.
J. Photochem Photobiol, A 1988, 44, 243.
"IUPAC Compendium of Chemical Terminology, 2$^{nd}$ Edition" 1997, HTTP://GOLDBOOK.IUPAC.ORG/B00744.

*Primary Examiner*—Susan W Berman
(74) *Attorney, Agent, or Firm*—Thibault Fayette; John G. Powell

(57) ABSTRACT

This invention is to provide an absorbent member and a method for making such an absorbent member. The absorbent member comprises modified water absorbent having good production efficiency, good absorbency against pressure, good absorption speed, gel strength, good liquid permeability, and the like. The modified water absorbent resin is made by a method, which comprises (i) a mixing step comprising mixing a water absorbent resin, water, and a water-soluble radical polymerization initiator without addition of an ethylenically unsaturated monomer, to obtain a water absorbent resin composition, and (ii) an irradiating step comprising irradiating said water absorbent resin composition obtained in the mixing step with active energy rays, wherein the surface water content of said water absorbent resin in said water absorbent resin composition at least at any point of time in the irradiating step (ii) is controlled to a level of not lower than 3.0% by weight based on 100% by weight of the water absorbent resin. Preferably, the amount of water mixed in said step (i) exceeds 20 parts by weight and is not more than 100 parts by weight based on 100 parts by weight of the water absorbent resin.

12 Claims, 1 Drawing Sheet

U.S. PATENT DOCUMENTS

| | | | |
|---|---|---|---|
| 4,950,683 A | 8/1990 | Ward et al. | |
| 4,950,692 A | 8/1990 | Lewis et al. | |
| 4,973,632 A | 11/1990 | Nagasuna et al. | |
| 4,985,518 A | 1/1991 | Alexander et al. | |
| 5,124,416 A | 6/1992 | Haruna et al. | |
| 5,128,386 A | 7/1992 | Rehmer et al. | |
| 5,137,537 A | 8/1992 | Herron et al. | |
| 5,145,906 A | 9/1992 | Chambers et al. | |
| 5,147,345 A | 9/1992 | Young et al. | |
| 5,151,092 A | 9/1992 | Buell et al. | |
| 5,164,459 A | 11/1992 | Kimura et al. | |
| 5,223,645 A | 6/1993 | Barwich et al. | |
| 5,244,735 A | 9/1993 | Kimura et al. | |
| 5,244,934 A | 9/1993 | Umeda et al. | |
| 5,248,805 A | 9/1993 | Boettcher et al. | |
| 5,250,640 A | 10/1993 | Irie et al. | |
| 5,260,345 A | 11/1993 | Desmarais et al. | |
| 5,264,495 A | 11/1993 | Irie et al. | |
| 5,264,533 A | 11/1993 | Rehmer et al. | |
| 5,275,773 A | 1/1994 | Irie et al. | |
| 5,342,338 A | 8/1994 | Roe | |
| 5,380,808 A | 1/1995 | Sumiya et al. | |
| 5,387,207 A | 2/1995 | Dyer et al. | |
| 5,389,699 A | 2/1995 | Rehmer et al. | |
| 5,397,316 A | 3/1995 | Lavon et al. | |
| 5,422,405 A | 6/1995 | Dairoku et al. | |
| 5,478,879 A | 12/1995 | Kajikawa et al. | |
| 5,554,145 A | 9/1996 | Roe et al. | |
| 5,562,646 A | 10/1996 | Goldman et al. | |
| 5,569,234 A | 10/1996 | Buell et al. | |
| 5,597,873 A | 1/1997 | Chambers et al. | |
| 5,610,208 A | 3/1997 | Dairoku et al. | |
| 5,625,222 A | 4/1997 | Yoneda et al. | |
| 5,633,316 A | 5/1997 | Gartner et al. | |
| 5,650,222 A | 7/1997 | DesMarais et al. | |
| 5,859,084 A | 1/1999 | Schroder et al. | |
| 5,883,158 A | 3/1999 | Nambu et al. | |
| 5,922,417 A | 7/1999 | Singleton et al. | |
| 5,976,696 A | 11/1999 | Collette et al. | |
| 6,004,306 A | 12/1999 | Robles et al. | |
| 6,007,833 A | 12/1999 | Chudzik et al. | |
| 6,043,311 A | 3/2000 | Houben et al. | |
| 6,222,091 B1 | 4/2001 | Beihoffer et al. | |
| 6,228,930 B1 | 5/2001 | Dairoku et al. | |
| 6,359,049 B1 | 3/2002 | Carrico et al. | |
| 6,376,072 B1 | 4/2002 | Evans et al. | |
| 6,455,600 B1 | 9/2002 | Hahnie et al. | |
| 6,562,879 B1 | 5/2003 | Hatsuda et al. | |
| 6,565,981 B1 | 5/2003 | Messner et al. | |
| 6,579,958 B2 | 6/2003 | Wilson | |
| 6,803,107 B2 | 10/2004 | Mitchell et al. | |
| 6,846,518 B2 | 1/2005 | Katoh et al. | |
| 7,098,284 B2 * | 8/2006 | Torii et al. | 526/317.1 |
| 7,166,356 B2 | 1/2007 | Flohr | |
| 7,183,336 B2 | 2/2007 | Berlin et al. | |
| 7,199,211 B2 | 4/2007 | Popp et al. | |
| 7,201,941 B2 * | 4/2007 | Irie et al. | 427/222 |
| 7,259,212 B2 | 8/2007 | Popp et al. | |
| 7,405,321 B2 | 7/2008 | Riegel et al. | |
| 7,420,013 B2 | 9/2008 | Riegel et al. | |
| 7,452,922 B2 | 11/2008 | Berlin et al. | |
| 7,504,551 B2 * | 3/2009 | Herfert et al. | 604/372 |
| 7,569,618 B2 * | 8/2009 | Flohr et al. | 522/3 |
| 7,576,138 B2 * | 8/2009 | Flohr et al. | 522/3 |
| 2002/0053754 A1 | 5/2002 | Katoh et al. | |
| 2003/0045847 A1 | 3/2003 | Whitmore et al. | |
| 2003/0135172 A1 | 7/2003 | Whitmore et al. | |
| 2003/0233082 A1 | 12/2003 | Kline et al. | |
| 2004/0137250 A1 | 7/2004 | Daniel et al. | |
| 2004/0140070 A1 | 7/2004 | Ponomarenko et al. | |
| 2004/0143030 A1 | 7/2004 | Ikkai | |
| 2004/0155383 A1 | 8/2004 | Jackson et al. | |
| 2004/0167486 A1 | 8/2004 | Busam et al. | |
| 2005/0003176 A1 | 1/2005 | Katoh et al. | |
| 2005/0048221 A1 | 3/2005 | Irie et al. | |
| 2005/0142965 A1 | 6/2005 | LaFortune | |
| 2005/0203474 A1 | 9/2005 | Flohr | |
| 2005/0215752 A1 | 9/2005 | Popp et al. | |
| 2005/0234410 A1 | 10/2005 | Ashton et al. | |
| 2006/0020078 A1 | 1/2006 | Popp et al. | |
| 2006/0052478 A1 | 3/2006 | Madsen et al. | |
| 2006/0089611 A1 | 4/2006 | Herfert et al. | |
| 2006/0128827 A1 * | 6/2006 | Matsumoto et al. | 522/150 |
| 2006/0212011 A1 | 9/2006 | Popp et al. | |
| 2006/0235141 A1 | 10/2006 | Riegel et al. | |
| 2006/0247377 A1 | 11/2006 | Riegel et al. | |
| 2007/0048516 A1 | 3/2007 | Flohr et al. | |
| 2007/0048517 A1 | 3/2007 | Flohr et al. | |
| 2007/0049689 A1 | 3/2007 | Meyer et al. | |
| 2007/0082142 A1 | 4/2007 | Flohr | |
| 2007/0167536 A1 | 7/2007 | Iwamura et al. | |
| 2007/0238806 A1 | 10/2007 | Mitsukami et al. | |

FOREIGN PATENT DOCUMENTS

| | | |
|---|---|---|
| EP | 0 700 673 A1 | 3/1996 |
| EP | 0 509 708 B1 | 12/1997 |
| EP | 811 636 B1 | 8/2001 |
| EP | 1 178 059 A2 | 2/2002 |
| EP | 1 199 327 A2 | 2/2002 |
| EP | 0 456 136 B1 | 3/2002 |
| EP | 1 302 485 A1 | 4/2003 |
| EP | 955 086 B1 | 9/2003 |
| EP | 0 844 270 B1 | 11/2004 |
| EP | 922 717 B1 | 1/2005 |
| EP | 1 504 771 A1 | 2/2005 |
| EP | 1 506 788 A | 2/2005 |
| EP | 1 516 884 A2 | 3/2005 |
| EP | 1 624 002 A | 2/2006 |
| EP | 1 757 646 A | 2/2007 |
| EP | 1 264 930 | 9/2008 |
| JP | 01-092226 A | 4/1989 |
| JP | 01-292103 | 11/1989 |
| JP | 2003-073919 | 3/2003 |
| JP | 2003 156961 A | 5/2003 |
| WO | WO 81/03274 A1 | 11/1981 |
| WO | WO 93/16131 A1 | 8/1993 |
| WO | WO 96/07380 | 3/1996 |
| WO | WO 99/55393 A | 11/1999 |
| WO | WO 0189591 A2 | 11/2001 |
| WO | WO 0189592 A2 | 11/2001 |
| WO | WO 02/094328 A | 11/2002 |
| WO | WO 02/100912 | 12/2002 |
| WO | WO 03/043670 A1 | 5/2003 |
| WO | WO-2004/031253 A1 | 4/2004 |
| WO | WO 2004/085496 A | 10/2004 |
| WO | WO 2005/014066 A1 | 2/2005 |
| WO | WO 2005/044915 A1 | 5/2005 |
| WO | WO 2005/082429 A2 | 9/2005 |
| WO | WO 2005/097313 A1 | 10/2005 |
| WO | WO 2006/062253 A1 | 6/2006 |
| WO | WO 2006/062258 A2 | 6/2006 |
| WO | WO 2006/063229 A2 | 6/2006 |

* cited by examiner

ABSORBENT MEMBER COMPRISING A MODIFIED WATER ABSORBENT RESIN

FIELD OF THE INVENTION

This invention relates to an absorbent member for use in absorbent articles, especially diapers and training pants. The absorbent member comprises a water absorbent resin made by a method comprising the step of irradiating a water absorbent resin with active energy rays.

BACKGROUND OF THE INVENTION

A water absorbent resin has been hitherto used as a component for hygienic materials such as sanitary cotton, disposable diaper, and absorbents for other kinds of body fluid. As typical examples of the water absorbent resin, hydrolyzate of starch-acrylonitrile graft polymer, neutralized starch-acrylic acid graft polymer, saponified vinyl acetate-acrylic ester copolymer, hydrolyzate of acrylonitrile copolymer or acrylamide copolymer, and cross-linked product thereof, and partially neutralized cross-linked acrylic acid may be cited. These water absorbent resins have an internal cross-linked structure and are in-soluble in water.

The characteristics of such a water absorbent resin include for example high absorption capacity, high absorption speed, high gel strength, and fully satisfactory suction power necessary for sucking water from a medium. The water absorbing properties are affected by cross-link density, and an increase in the cross-link density typically leads to an increase in the gel strength but a decrease in the amount of water absorbed. Particularly, increased absorption capacity typically leads to reduced absorption speed, reduced gel strength, and reduced suction power, for example. The water absorbent resin having improved absorption capacity, therefore, would possibly induce inhomogeneous absorption of water and lead to aggregation of absorbent particles when the water absorbent resin particles contact with water, and also induce dramatic decrease in absorption speed because the water is not diffused throughout the entire volumes of water absorbent resin particles.

For obtaining a water absorbent resin having high absorption capacity and a comparatively satisfactory absorption speed, a method for coating a surface of water absorbent resin particles with a surfactant or a nonvolatile hydrocarbon has been available. This method indeed can exalt the dispersibility of initially absorbed water but does not have sufficient effects on enhancing absorption speed and suction power of individual resin particles.

As a means to produce a polyacrylic acid based water absorbent polymer having improved water absorbing properties, a method which comprises heating an aqueous composition of a polymer having a partial alkali metal salt of polyacrylic acid as a main component and having a low cross-link density in the presence of a water-soluble peroxide radical initiating agent thereby introducing a cross-link therein by radical cross-linking has been proposed (U.S. Pat. No. 4,910,250). It is difficult to distribute uniformly internal cross-links in the polymer and uneasy to adjust the cross-link density. Accordingly, a polymer which contains water-soluble polyacrylic acid gel having low cross-link density is obtained and then the polymer is heated together with a persulfate added thereto as a polymerization initiator. U.S. Pat. No. 4,910,250 states that excellent water absorbing properties can be attained and a water absorbent resin having no stickiness can be obtained because the adjustment of the amount of the initiator to be added can allow precise control of cross-link density and uniform presence of cross-link in the polymer.

While the persulfate which is used in the U.S. Pat. No. 4,910,250 is decomposed by heat, it is also decomposed by ultraviolet rays to generate radicals (J. Phys. Chem., 1975, 79, 2693, J. Photochem. Photobiol., A. 1988, 44, 243). Since the persulfate acts as a polymerization initiator, the aqueous solution of a water-soluble vinyl monomer, when exposed to radiation, undergoes polymerization and radical cross-linking simultaneously (JP-A 2004-99,789). A reaction system has also been known, which comprises adding a hydrophilic polymer component and a photo-polymerization initiator, further adding a cross-linking agent thereto, and irradiating them with ultraviolet rays to form an internal cross-link (WO 2004/031253).

Further, a method which comprises treating a surface of a water absorbent resin to increase cross-link density of the surface of water absorbent resin has also been known (U.S. Pat. Nos. 4,666,983 and 5,422,405, for example). Such water absorbent resins as cited in the preceding publications comprise a reactive functional group on their surfaces. By adding a surface cross-linking agent capable of reacting with the functional groups in order to introduce cross-links between the functional groups, cross-link density on the surface of water absorbent resin can be increased and a water absorbent resin having excellent water absorbing properties even under pressure can be obtained.

Further, since the use of the surface cross-linking agent requires a high temperature and a long time for the reaction of forming cross-link and entails the problem of suffering persistence of unaltered cross-linking agent, a method which comprises contacting an aqueous solution containing a peroxide radical initiating agent with a resin, heating the resin to decompose the radical initiating agent and introduce cross-links into polymer molecular chains in the neighborhood of the surface of the resin has been proposed (U.S. Pat. No. 4,783,510). In the working example, a water absorbent resin exhibiting exalted absorption capacity was obtained by heating with superheated steam at 130° C. for 6 minutes.

SUMMARY OF THE INVENTION

The present invention refers to an absorbent member for use in absorbent articles, the absorbent member comprising modified water absorbent resin. The water absorbent resin is made by a method comprising:
(i) a mixing step comprising mixing water absorbent resin, water, and a water-soluble or a heat-degradable radical polymerization initiator without addition of an ethylenically unsaturated monomer, to obtain a water absorbent resin composition; and
(ii) an irradiating step comprising irradiating said water absorbent resin composition obtained in the mixing step with active energy rays, wherein the surface water content of said water absorbent resin in said water absorbent resin composition at least at any point of time in the irradiating step (ii) is controlled to a level of not lower than 3.0% by weight based on 100% by weight of the water absorbent resin.

Preferably, the amount of water mixed in step (i) exceeds 20 parts by weight and is not more than 100 parts by weight based on 100 parts by weight of the water absorbent resin.

The present invention further refers to a method of making such absorbent members and modifications of making the absorbent members of claim 1 to 3 as set out in the following description and in the dependent claims.

DETAILED DESCRIPTION OF THE INVENTION

Figure 1:
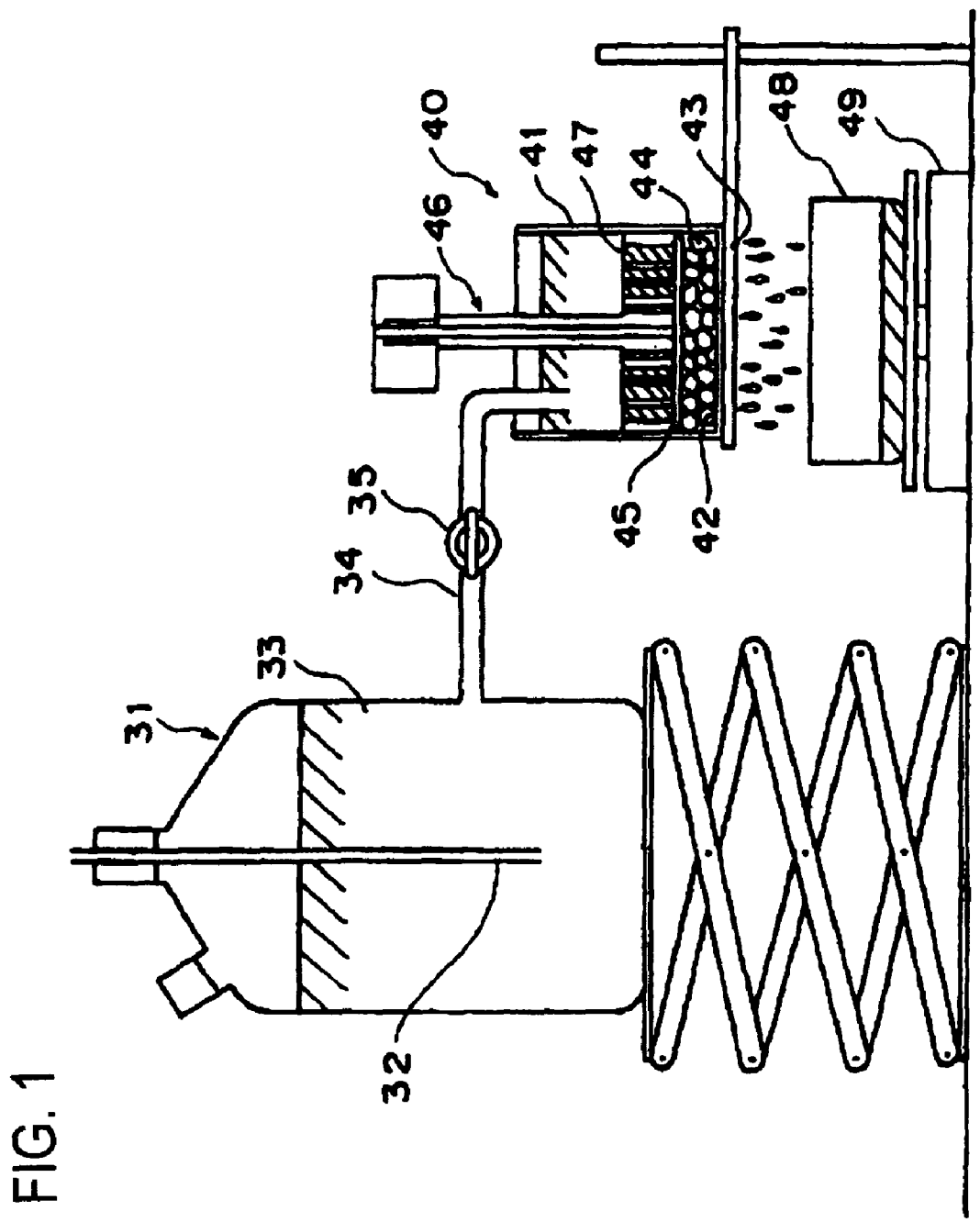
FIG. 1 is a schematic diagram of a measuring device to be used in determining the saline flow conductivity (SFC).

The object of surface cross-linking a water absorbent resin is achieved by a method for producing a water absorbent resin having an improved balance between absorption capacity and absorption speed. Generally, this object requires a cross-linking agent having at least two functional groups capable of reacting with the functional group present on the surface of the water absorbent resin. As typical examples of the cross-linking agent, polyhydric alcohols, polyvalent glycidyl ethers, haloepoxy compounds, polyvalent aldehydes, polyvalent amines, and polyvalent metal salts may be cited. Since the cross-linking agent has low reactivity, the relevant reaction is required to be carried out at an elevated temperature and occasionally to be retained in a heated state for a long time. The reaction, therefore, requires relatively high amounts of energy and time.

This invention aims at providing a method for an efficient production of a water absorbent resin having good absorbency against pressure, absorption speed, gel strength, and permeability of liquid.

It has been found that surfaces of the particles need to retain water to some extent in order to effectively introduce a cross-linking structure on surfaces of water absorbent resin particles. Namely, it has been found that in conventional methods, when surfaces of the particles are not humid to some extent, introduction of a cross-linking structure on surfaces of particles cannot effectively be attained, and therefore a water absorbent resin having good water absorbent properties cannot be produced. Based on this finding, the present inventors have attempted to conduct surface treatment of water absorbent resin particles being humid to some extent. In addition, the present inventors have also found that surface cross-linking efficiency and water absorbent properties of the resultant water absorbent resin can be improved, by irradiation with active energy rays without using conventional addition of a surface cross-linking agent. Namely, herein a method for the production of a modified water absorbent resin is provided, which comprises (i) a mixing step comprising mixing a water absorbent resin, water, and a water-soluble radical polymerization initiator without addition of an ethylenically unsaturated monomer, to obtain a water absorbent resin composition, and (ii) an irradiating step comprising irradiating said water absorbent resin composition obtained in the mixing step with active energy rays, wherein the surface water content of said water absorbent resin in said water absorbent resin composition at least at any point of time during the irradiating step (ii) is controlled to a level of not lower than 3.0% by weight based on 100% by weight of the water absorbent resin. Preferably, the amount of water mixed in step (i) exceeds 20 parts by weight and is not more than 100 parts by weight based on 100 parts by weight of the water absorbent resin.

According to the method of this invention, a uniform cross-linking structure can be introduced on a surface of water absorbent particles. As a result, the obtained water absorbent resin has good absorption capacity, good absorption speed, good gel strength, and good suction power.

Since the method of this invention for the production of a modified water absorbent resin achieves surface cross-linking by irradiation with active energy rays, the water absorbent resin can be modified in a shorter period as compared with the conventional method.

The method for the production of a modified water absorbent resin comprised in the absorbent members according to this invention will be described in detail below.

(a) Water Absorbent Resin

The water absorbent resin which can be used in this invention is a water-swellable, water-insoluble, cross-linked polymer which can form a hydrogel. The term "ability to swell in water" as used in this invention refers to the free swelling capacity of a given sample in an aqueous 0.9% by weight sodium chloride solution (physiological saline), i.e. the ability of the sample to absorb the physiological saline essentially not lower than 2 g/g and preferably in the range of from 5 to 100 g/g and more preferably in the range of from 10 to 60 g/g. The term "insoluble in water" as used herein means that an uncross-linked water-soluble component (a water-soluble polymer; hereinafter also called as "an elutable and soluble portion") in the water absorbent resin, which is preferably in the range of from 0 to 50% by weight, more preferably not more than 25% by weight, still more preferably not more than 15% by weight, and particularly preferably not more than 10% by weight. In this connection, as a value of centrifuge retention capacity, a value measured by the method specified in the working example cited below is adopted. And as a value of an elutable and soluble portion, a value measured by a method described below is adopted.

Method for Measuring an Elutable and Soluble Portion

In a covered plastic container (with a diameter of 6 cm and a height of 9 cm) having a volume of 250 ml, 184.3 g of physiological saline is placed, 1.00 g of water absorbent resin is added. An elutable and soluble portion in a resin is extracted by stirring the mixture for 16 hours with a magnetic stirrer having a diameter of 8 mm and a length of 25 mm at a rotation speed of 500 rpm. This extract is filtrated with one sheet of a filter paper (0.26 mm in thickness and 5 μm in retained particle diameter; made by Advantec Toyo K.K. and sold under the product name of "JIS P 3801 No. 2"). Then, 50.0 g of the resultant filtrate is taken to make a solution for measuring.

First, only physiological saline is titrated with 0.1 N of an aqueous solution of sodium hydroxide to pH 10. Then, it is titrated with 1 N of an aqueous solution of hydrochloric acid to pH 2.7, to obtain comparative (blank) titration amounts (called as [bNaOH] and [bHCl], respectively).

By conducting the same operation of titration with the solutions for measuring, titration amounts (called as [NaOH] and [HCl], respectively) were obtained. For instance, in the case of a water absorbent resin consisting of known amounts of acrylic acid and sodium salt thereof, an elutable and soluble portion in the water absorbent resin can be calculated on the basis of an average molecular weight of the monomers and the titration amounts obtained by the above described operation in accordance to the equation described below. In the case of an unknown amount, an average molecular weight of a monomer is calculated, by using a neutralization ratio obtained by titration according to the equation described below.

Elutable and soluble portion (% by weight) =

0.1 × (Average molecular weight of monomer) ×

184.3 × 100 × ([HCl] − [bHCl]) / 1000 / 1.0 / 50.0

Neutralization ratio (% by mol) = [1 −

([NaOH] − [bNaOH]) / ([HCl] − [bHCl])] × 100

As used herein, the term "modification" refers to all physical or chemical actions performed on a given water absorbent resin, including surface cross-linking, formation of pores therein, and imparting hydrophilic or hydrophobic property thereto, for example.

The water absorbent resin which can be used in this invention is not particularly restricted but is only required to be capable of being obtained by polymerizing a monomer component essentially containing an ethylenically unsaturated monomer by means of any of the known methods.

The ethylenically unsaturated monomer is not particularly restricted but is preferred to be a monomer having an unsaturated double bond at the terminal thereof. Typical examples thereof are, anionic monomers such as (meth)acrylic acid, 2-(meth)acryloyl ethane sulfonic acid, 2-(meth)acryloyl propane sulfonic acid, 2-(meth)acrylamide-2-methyl propane sulfonic acid, vinyl sulfonic acid, and styrene sulfonic acid, and salts thereof; nonionic hydrophilic group-containing monomers such as (meth)acrylamide, N-substituted (meth)acrylamide, 2-hydroxyethyl(meth)acrylate, and 2-hydroxypropyl(meth)acrylate; and amino group-containing unsaturated monomers such as N,N-dimethylaminoethyl(meth)acrylate, N,N-diethylaminoethyl(meth)acrylate, N,N-diethylaminopropyl(meth)acrylate, and N,N-dimethylaminopropyl(meth)acrylamide, and quaternized products thereof. These monomers may be used either singly or in the form of a mixture of two or more members. Among monomers cited above, (meth)acrylic acid, 2-(meth)acryloyl ethane sulfonic acid, 2-(meth)acrylamide-2-methylpropane sulfonic acid, and salts thereof, N,N-dimethylaminoethyl (meth)acrylate and quaternized N,N-dimethylaminoethyl (meth)acrylate, and (meth)acrylamide prove preferable, and acrylic acid and/or the salt thereof are particularly preferable.

When an acrylic acid salt is used as the monomer, the monovalent salt of acrylic acid selected among alkali metal salt, ammonium salt, and amine salt of acrylic acid may be preferably used. More preferably, alkali metal salts of acrylic acid may be used, and acrylic acid salts selected among sodium salt, lithium salt, and potassium salt thereof may be particularly preferably used.

In the production of a water absorbent resin, a monomer component other than the monomers cited above may be used in such an amount as to impair effects of this invention. As typical examples of such other monomer components, hydrophobic monomers such as aromatic ethylenically unsaturated monomers having from 8 to 30 carbon atoms, aliphatic ethylenically unsaturated monomers having from 2 to 20 carbon atoms, alicyclic ethylenically unsaturated monomers having from 5 to 15 carbon atoms, and alkyl esters of (meth)acrylic acid containing alkyl groups having from 4 to 50 carbon atoms may be cited. The proportion of such a hydrophobic monomer is generally in the range of from 0 to 20 parts by weight, based on 100 parts by weight of the ethylenically unsaturated monomer. If the proportion of the hydrophobic monomer exceeds 20 parts by weight, water absorbing properties of the produced water absorbent resin would be degraded.

The water absorbent resin which can be used in this invention is insolubilized by the formation of an internal cross-link. This internal cross-link may be of self-cross-linking type using no cross-linking agent, or alternatively can be formed by using an internal cross-linking agent having not less than two polymerizable unsaturated groups and/or not less than two reactive functional groups in one molecular unit.

The internal cross-linking agent is not particularly restricted. As typical examples of the inner cross-linking agent, N,N'-methylenebis(meth)acrylamide, N-methylol (meth)acrylamide, glycidyl(meth)acrylate, (poly)ethylene glycol di(meth)acrylate, (poly)propylene glycol di(meth) acrylate, glycerin tri(meth)acrylate, glycerin acrylate methacrylate, polyvalent metal salts of (meth)acrylic acid, trimethylol propane tri(meth)acrylate, triallyl amine, triallyl cyanurate, triallyl isocyanurate, triallyl phosphate, ethylene glycol diglycidyl ether, (poly)glycerol glycidyl ether, and polyethylene glycol diglycidyl ether may be cited. These internal cross-linking agents may be used singly or in the form of a mixture of two or more members.

The amount of the internal cross-linking agent to be used is preferably in the range of from 0.0001 to 1 mol %, more preferably from 0.001 to 0.5 mol %, and still more preferably from 0.005 to 0.2 mol %, based on the total amount of monomer components used in the production of a water absorbent resin. If this amount is less than 0.0001 mol %, the internal cross-linking agent may not be introduced satisfactorily into the resin. Conversely, if the amount exceeds 1 mol %, gel strength of the water absorbent resin may be too high and the absorption capacity may consequently be too low. For the introduction of a cross-linked structure into an interior of the polymer by using the internal cross-linking agent, the internal cross-linking agent can be added to the reaction system prior to, during, or after the polymerization of monomers, or after the neutralization of the produced polymer.

For the purpose of producing a water absorbent resin, monomer components including the monomers and the internal cross-linking agent as mentioned above are polymerized in an aqueous solution form. Suitable polymerization initiators include for example water-soluble radical polymerization initiators such as persulfates such as potassium persulfate, ammonium persulfate, and sodium persulfate; potassium peracetate, sodium peracetate, potassium percarbonate, sodium percarbonate, and t-butyl hydroperoxide; hydrogen peroxide; azo compounds such as 2,2'-azobis(2-amidinopropane)-dihydrochloride, and photopolymerization initiators such as 2-hydroxy-2-methyl-1-phenyl-propan-1-one. The water-soluble radical polymerization initiators may be combined with a reducing agent such as a sulfite, L-ascorbic acid, or a ferric salt, to be used as a redox type initiator.

The concentration of the monomer in the aqueous monomer solution is not particularly restricted but is preferably within the range of from 15 to 90% by weight, and more preferably from 35 to 80% by weight. If this concentration is less than 15% by weight, a lot of heat and time would be required for drying because the resultant hydrogel has an unduly large content of water.

A method for the polymerization is not particularly restricted but may be selected among well-known methods such as solution polymerization, reversed-phase suspension polymerization, precipitation polymerization, and bulk polymerization. Among these methods, the aqueous solution polymerization which comprises dissolving a monomer in an aqueous solution and polymerizing it in the aqueous solution, and the reversed phase suspension polymerization may be particularly advantageous due to the ease of control of polymerization reaction and the performance of a produced water absorbent resin.

In initiating the polymerization, the polymerization initiator is used to start the polymerization. Besides the polymerization initiator, active energy rays such as ultraviolet rays, electron radiation, and γ rays may be used either singly or in combination with a polymerization initiator. Though the temperature in initiating the polymerization depends on the kind of polymerization initiator used, it is preferably in the range of from 15 to 130° C., and more preferably from 20 to 120° C. If the temperature in initiating the polymerization deviates from the range mentioned above, this may result increased amounts of residual monomer in the produced water absorbent resin. Also, self cross-linking may proceed excessively, consequently degrading water absorbing properties of the produced water absorbent resin.

The "reversed phase suspension polymerization" is a method of polymerization in which an aqueous monomer solution is suspended in a hydrophobic organic solvent. It is disclosed in U.S. Pat. Nos. 4,093,776, 4,367,323, 4,446,261, 4,683,274, and 5,244,735, for example. The "aqueous solution polymerization" is a method for polymerizing an aqueous monomer solution without using a dispersing solvent. It is disclosed in U.S. Pat. Nos. 4,625,001, 4,873,299, 4,286,082, 4,973,632, 4,985,518, 5,124,416, 5,250,640, 5,264,495, 5,145,906, and 5,380,808, and European Patent Nos. 0 811 636, 0 955 086, and 0 922 717, for example. The monomers and the initiators which are cited by way of illustration in these methods of polymerization can be applied to this invention.

The aqueous solution polymerization may be performed by polymerizing partially neutralized acrylic acid or by polymerizing an acid group-containing monomer such as acrylic acid and the like and subsequently neutralizing the resultant polymer with such an alkali compound as sodium hydroxide or sodium carbonate. Accordingly, the water absorbent resin to be used in this invention preferably has an acid group and a specific neutralization ratio (mol % of the neutralized acids group in the whole of acid groups). In this case, the neutralization ratio of the produced water absorbent resin (mol % of the neutralized acids group in the whole of acid groups) is in the range of from 25 to 100 mol %, and preferably from 50 to 90 mol %, more preferably of from 50 to 75 mol %, and most preferably from 60 to 70 mol %.

Accordingly, the preferable embodiment of this invention is to provide a method for the production of a modified water absorbent resin, which comprises (i) mixing a water absorbent resin, water, and persulfate as a radical polymerization initiator without addition of an ethylenically unsaturated monomer and (ii) irradiating the resultant mixture with active energy rays, wherein the water absorbent resin contains an acid group and has a neutralization ratio (mol % of the neutralized acids group in the whole of acid groups) in the range of 50 to 75 mol %. After the completion of the polymerization, a hydrogel-like cross-linked polymer is obtained. While this invention permits this hydrogel-like cross-linked polymer in its unaltered form as a water absorbent resin, the polymer is preferably dried so as to give a water content (% by weight) [100−(Solid content) (% by weight)] which will be specifically described herein below.

Incidentally, in this invention, a water absorbent resin composition is obtained by mixing a water absorbent resin, a water-soluble radical polymerization initiator and/or a heat-degradable radical polymerization initiator (in the present specification, referred collectively to as "radical polymerization initiator"), and water, which will be described specifically herein below. Then, the resultant composition is irradiated with active energy rays to modify the water absorbent resin. This modification results from the action of active radicals generated from the polymerization initiator on the main chain of the polymer. This modification, therefore, does not need to be limited to water absorbent resin which is obtained by polymerizing a water-soluble ethylenically unsaturated monomer as described above but may be effected on such a water absorbent resin as cross-linked polyvinyl alcohol, cross-linked polyethylene oxide, cross-linked polyaspartic acid, and cross-linked carboxymethyl cellulose, for example.

The water absorbent resin which can be used in this invention is preferably a powdery water absorbent resin which is obtained by polymerizing a monomer having acrylic acid (salt) particularly as its main component. The hydrogel-like polymer which is obtained by polymerization is preferably dried and subsequently pulverized to a water absorbent resin. The drying may be effected by using a drier such as a hot air drier at a temperature in the range of from 100 to 220° C., and more preferably from 120 to 200° C.

For pulverization, among shear primary crushers, impact shredders, and high speed rotary grinders included in the names of the powdering machines classified in Table 1.10 of Particle Technology Handbook (first edition, compiled by Particle Technology Association), the powdering machines having at least one of the powdering mechanisms such as cutting, shearing, striking, and rubbing can be adopted particularly favorably. Among the powdering machines, the powdering machines which have cutting and shearing as main mechanisms can be used particularly advantageously. A roll mill (roll rotary type) powdering machine may be cited as a preferred example.

The water absorbent resin which can be used in this invention is preferably in a powdery form. More preferably, it is a powdery water absorbent resin which contains particles of a diameter in the range of from 150 to 850 μm (as defined by sieve classification) in a proportion in the range of from 90 to 100% by weight, and particularly preferably from 95 to 100% by weight. When the modified water absorbent resin having a particle diameter exceeding 850 μm is used in disposable diapers, for example, it may rupture the top sheet of a diaper. If the particles of a diameter smaller than 150 μm in a proportion exceeding 10% by weight based on weight of the water absorbent resin, the fine particles may scatter and clog the texture while in use and would degrade water absorbing properties of the modified water absorbent resin. The weight average particle diameter of the water absorbent resin may be in the range of from 10 to 1,000 μm, and preferably from 200 to 600 μm. If the weight average particle diameter is less than 10 μm, this may possibly result in drawbacks regarding safety and health. Conversely, if it exceeds 1,000 μm, the water absorbent resin may not be well-suited for use in disposable diapers, for example. In this connection, as a value of the particle diameter, a value measured by a measuring method of a particle size distribution specified in the working example cited below is adopted.

In addition or alternatively, the water absorbent resin to be used in this invention is preferably obtained by producing a water absorbent resin precursor having a low neutralization ratio, and mixing the water absorbent resin precursor with a base. A multifunctional surface-treatment agent has been conventionally used for the surface-treatment (surface cross-linking). The multifunctional surface-treatment agent serves to react with a carboxyl group (—COOH) in a water absorbent resin but do not react with the salt thereof (for example, —COONa). Accordingly, uniform cross-linking can be attained by preparing an ethylenically unsaturated monomer mixture (for example, a mixture of acrylic acid with sodium acrylate) in which —COOH/—COONa ratio has been adjusted within a suitable range in advance, polymerizing the resultant mixture to produce a water absorbent resin having the —COOH and —COONa groups uniformly distributed therein, and subjecting the resultant water absorbent resin to surface cross-linking with a multifunctional surface-treatment agent. On the other hand, when a water absorbent resin is obtained by polymerizing a monomer mixture including an acid type ethylenically unsaturated monomer like acrylic acid as a main component, and then neutralizing the resultant polymer with an alkali compound such as sodium hydroxide and sodium carbonate, the resultant water absorbent resin has a small elutable portion and high gel strength. However, when subjected to surface cross-linking with a multifunctional surface-treatment agent, the absorbent resin likely has degraded water absorbency, because the —COOH and —COONa groups are not uniformly distributed in the water absorbent resin. Accordingly, the water absorbent resin to be produced by the latter method is not desirably subjected to such a conventional surface cross-linking with a multifunctional surface-treatment agent. Conversely, according to the method of this invention, since a water-soluble radical polymerization initiator or a heat-degradable radical polymerization initiator induces cross-linking by extracting a hydrogen in a main chain to form a radical and using the radical for coupling, but not by reacting with —COOH, the cross-linking reaction is not affected by whether or not —COOH groups are uniformly distributed in the water absorbent resin. As a result, according to the method of this invention, a water absorbent resin is obtained by polymerizing a monomer or a monomer mixture including as a main component an acid type ethylenically unsaturated monomer like acrylic acid to obtain a water absorbent resin precursor having a low neutralization ratio. This water absorbent resin precursor is then neutralized with an alkali compound such as sodium hydroxide and sodium carbonate, and the resultant modified water absorbent yields high gel strength and good water absorbency.

If a water absorbent resin precursor having a low neutralization ratio is obtained by polymerizing a monomer or a monomer mixture including as a main component an acid type ethylenically unsaturated monomer, and then adding a base to the water absorbent resin precursor, the base may be added either in a solid form or in a liquid form. Preferably, the base is added in a liquid form, particularly in an aqueous solution form. When the base is added in an aqueous solution form, adding a base to a water absorbent resin precursor and producing a water absorbent resin composition can done simultaneously. The base which can be used in this embodiment is not particularly limited so long as it permits the neutralization of the water absorbent resin precursor having a low neutralization ratio to a desired neutralization ratio. Well-known inorganic and organic salt and acid can be used, such as sodium hydroxide, potassium hydroxide, lithium hydroxide, ammonium hydroxide, sodium carbonate, potassium carbonate, ammonium carbonate, sodium bicarbonate, potassium bicarbonate, ammonium bicarbonate, sodium phosphate, potassium phosphate, ammonium phosphate, sodium borate, potassium borate, ammonium pentaborate, sodium acetate, potassium acetate, ammonium acetate, sodium lactate, potassium lactate, ammonium lactate, sodium propionate, potassium propionate, ammonium propionate. These bases can be used singly or in mixed form of two or more members. If a water absorbent resin precursor having a low neutralization ratio is obtained by polymerizing, suitable monomers are an acid type ethylenically unsaturated monomer such as acrylic acid, hydroxide of monovalent cation such as sodium hydroxide, potassium hydroxide, lithium hydroxide, and ammonium hydroxide; and carbonate of monovalent cation such as sodium carbonate, potassium carbonate, ammonium carbonate, sodium bicarbonate, potassium bicarbonate, and ammonium bicarbonate or mixtures thereof. Suitable monomers should have good physical properties, and permit efficient adjustment of neutralization ratio to a desired level. In this embodiment, the amount of base added is not particularly limited and can be suitably selected so that the water absorbent resin used in the mixing step (i) has a desired neutralization ratio adjusted within the preferable range as mentioned above.

In this invention, the expression "water absorbent resin precursor having a low neutralization ratio" is referred to as a water absorbent resin precursor having a low neutralization ratio (mol % of the neutralized acids group in the whole of acid groups) or having no neutralized acid groups (i.e., the neutralization ratio is zero), and typically referred to as a water absorbent resin precursor having a neutralization ratio (mol % of the neutralized acids group in the whole of acid groups) of from 0 to 50 mol %, more preferably from 0 to 20 mol %. Such a water absorbent resin precursor having a low neutralization ratio can be obtained by the same method as mentioned above by using a monomer mixture including as a main component an acid group-containing monomer like acrylic acid wherein a neutralization ratio is preferably adjusted within the above range.

The water content of the water absorbent resin prior to the modification to be used in the method for production of a modified water absorbent resin contemplated by this invention has no particular restriction so long as the water absorbent resin has fluidity. The water absorbent resin after being dried at 180° C. for three hours has a water content falling in the preferable range of from 0 to 50% by weight, from 0 to 40% by weight, from 0 to 30% by weight, from 0 to 20% by weight, from 0 to 10% by weight, and more preferably from 0 to 5% by weight in this order.

The water absorbent resin to be used in this invention is not limited to the product of the method as described above but may be any product obtained by some other method. While the water absorbent resin which is obtained by the method described above is a water absorbent resin having undergone no surface cross-linking, for use in the method for producing a modified water absorbent resin of this invention, the water absorbent resin which has undergone surface cross-linking in advance with a polyhydric alcohol, a polyvalent epoxy compound, an alkylene carbonate, or an oxazolidone compound can be adopted.

(b) Water Absorbent Resin Composition

In a method for the production of a modified water absorbent resin according to the present invention, in the step (i), a water absorbent resin composition is obtained by mixing water and a radical polymerization initiator (a water-soluble radical polymerization initiator and/or a heat-degradable radical polymerization initiator) with the water absorbent resin, without addition of an ethylenically unsaturated monomer.

Hitherto, the surface cross-linking of a water absorbent resin has been generally effected by using a surface cross-linking agent. The incorporation of the surface cross-linking agent results in strong, chemical binding between the functional groups present on the surface of resin and the surface cross-linking agent, thereby introducing a stable surface cross-link structure into the resin surface. Then, by properly selecting a chain length of the surface cross-linking agent, the distance between cross-links can be adjusted easily. By adjusting an amount of the surface cross-linking agent to be incorporated, the cross-link density can be controlled. This invention, however, permits the modification of a water absorbent resin, specifically the introduction of a cross-link structure to the surface of the water absorbent resin, by merely using a radical polymerization initiator without requiring the incorporation of the surface cross-linking agent. Further, by additionally adding water to obtain a water absorbent composition and irradiating the water absorbent resin composition with active energy rays, a cross-linked structure can be effectively introduced to the surface of the water absorbent resin particles and at the same time, the produced modified water absorbent resin has improved water absorption properties. Moreover, the addition of water in a relatively large amount to the water absorbent resin in the step (i) permits the efficient introduction of a cross-linking structure on a surface of the water absorbent resin in the step (ii) described in detail below, and thus also results in shortened irradiation time required for improving absorbency against pressure (AAP) and the saline flow conductivity (SFC) of the modified water absorbent resin to a desired level.

This invention uses the expression "without addition of an ethylenically unsaturated monomer" with the object of preventing a radical polymerization initiator from reacting with an ethylenically unsaturated monomer to avoid the consumption of the radical polymerization initiator that is activated by the irradiation with active energy rays prior to the action on the surface of the water absorbent resin in the step (ii).

In the step (i), water is mixed with a water absorbent resin. In this case, mixing of a water absorbent resin and water may be conducted by adding water alone, or by adding water in a form of an aqueous solution containing another component. As the aqueous solution, for example, an aqueous solution containing a radical polymerization initiator, an aqueous solution containing a mixing aid, and the like may be included.

In the step (i), the amount of water mixed with a water absorbent resin preferably exceeds 20 parts by weight and is not more than 100 parts by weight, based on 100 parts by weight of the water absorbent resin (as reduced to as 100 parts by weight of a solid content). The addition of water in a relatively large amount to the water absorbent resin in the step (i) permits the efficient introduction of a cross-linking structure on a surface of the water absorbent resin in the step (ii) described in detail below, and thus a shortened irradiation time. The preferable amount of water mixed with the water absorbent resin exceeds 20 parts by weight and is not more than 70 parts by weight, or exceeds 20 parts by weight and is not more than 50 parts by weight, or exceeds 20 parts by weight and is not more than 40 parts by weight, or exceeds 20 parts by weight and is not more than 30 parts by weight, in this order, based on 100 parts by weight of a water absorbent resin (referred to 100 parts by weight of a solid content). If the amount of water exceeds 100 parts by weight, a large amount of energy may be necessary during a drying step after irradiation with active energy rays. In addition, the water absorbent resin may possibly be decomposed.

Further, in step (i), in addition to the water, a water-soluble radical polymerization initiator and/or a heat-degradable radical polymerization initiator are mixed as a radical polymerization initiator with the water absorbent resin composition. Incidentally, hereinafter, "a water-soluble radical polymerization initiator and/or a heat-degradable radical polymerization initiator" are sometimes called collectively as radical polymerization initiator.

In this step, when "a water-soluble radical polymerization initiator" is mixed with a water absorbent resin, the initiator can be easily dispersed uniformly on the surface of the water absorbent resin which excels in hydrophilic property and water absorbing property. Thus, a water absorbent resin excelling in water absorbing properties can be produced.

The water-soluble radical polymerization initiator to be used in this invention has solubility in water (25° C.) of not less than 1% by weight, preferably not less than 5% by weight, and more preferably not less than 10% by weight. Typical examples are, persulfates such as ammonium persulfate, sodium persulfate, and potassium persulfate; hydrogen peroxide; and water-soluble azo compounds such as 2,2'-azobis-2-amidinopropane dihydrochloride and 2,2'-azobis[2-(2-imidazolin-2-yl)propane]dihydrochloride. The use of a persulfate is particularly preferable as the modified water absorbent resin has good water absorption properties including absorbency of physiological saline against pressure (in this specification, referred simply to as "absorbency against pressure"), and saline flow conductivity.

The term heat-degradable radical polymerization initiator to be used in this invention is a compound which generates a radical by heating. A heat-degradable radical polymerization initiator having 10 hour half-life decomposition temperature in the range of 0 to 120° C., more preferably 20 to 100° C., may be preferably used in this invention. In consideration of temperature during the irradiation with active energy rays, a heat-degradable radical polymerization initiator having 10 hour half-life decomposition temperature in the range of 40 to 80° C. can be particularly preferably used in this invention. If the lower limit of 10 hour half-life decomposition temperature is less than 0° C. (lower limit), the heat-degradable radical polymerization initiator would be too unstable during storage. Conversely, if the upper limit thereof exceeds 120° C. (upper limit), the chemical stability of the heat-degradable radical polymerization initiator may be too high.

In the step, when "a heat-degradable radical polymerization initiator" is mixed with a water absorbent resin, the surface modification can be carried out at a low temperature for a short period of time, and the resultant modified water absorbent resin can manifest high gel strength and good water-absorbing properties. The heat-degradable radical polymerization initiator to be used in this invention may be either oil-soluble or water-soluble. The decomposition rate of an oil-soluble heat-degradable radical polymerization initiator is less sensitive to a pH value and ion strength as compared to that of a water-soluble heat-degradable radical polymerization initiator. However, a water-soluble heat-degradable radical polymerization initiator may be more preferably used in respect of its permeability to a water absorbent resin because the water absorbent resin is hydrophilic.

The heat-degradable radical polymerization initiator is relatively inexpensive and the process and devices for the production thereof can be simplified because the strict light-shielding is not always required, as compared to a compound which has been commercially available as a photo-degradable radical polymerization initiator. Representative examples of the heat-degradable radical polymerization initiator are persulfates such as sodium persulfate, ammonium persulfate, and potassium persulfate; percarbonates such as sodium percarbonate; peracetates such as peracetic acid, and sodium peracetate; hydrogen peroxide; and azo compounds such as 2,2'-azobis(2-amidinopropane)dihydrochloride, 2,2'-azobis[2-(2-imidazolin-2-yl)propane]dihydrochloride, and 2,2'-azobis(2-methylpropionitrile. Among the heat-degradable radical polymerization initiators cited above, persulfates including sodium persulfate, ammonium persulfate, and potassium persulfate, and azo compounds including 2,2'-azobis(2-amidinopropane)dihydrochloride, 2,2'-azobis[2-(2-imidazolin-2-yl)propane]dihydrochloride, and 2,2'-azobis(2-methylpropionitrile) which have 10 hour half-life decomposition temperature in the range of 40 to 80° C. can be used preferably. Particularly, persulfates may be preferably used in respect of excellent absorbency of physiological saline against pressure, saline flow conductivity, and free swelling capacity.

The amount of the radical polymerization initiator is preferably in the range of from 0.01 to 20 parts by weight, more preferably from 0.1 to 15 parts by weight, and particularly preferably from 1 to 10 parts by weight, based on 100 parts by weight of the water absorbent resin. If the amount of the radical polymerization initiator to be mixed is less than 0.01 parts by weight, the water absorbent resin may not be sufficiently modified even upon exposure to the active energy rays. Conversely, if the amount of the radical polymerization initiator to be mixed exceeds 20 parts by weight, water absorbing properties of the modified water absorbent resin may possibly be degraded.

In this invention, by essentially using the water-soluble radical polymerization initiator and/or a heat-degradable radical polymerization initiator, excellent properties can be accomplished compared to cases wherein such radical polymerization initiators are omitted, for example, the case of using solely an oil-soluble photopolymerization initiator. Incidentally, the term "oil-soluble photopolymerization initiator" as used herein means a compound having water-solubility of less than 1% by weight.

While this invention essentially uses a water-soluble radical polymerization initiator and/or a heat-degradable radical polymerization initiator, an initiator other than the radical polymerization initiator can be additionally used. As typical examples of the other polymerization initiators which can be additionally used, are photopolymerization initiators such as oil-soluble benzoin derivatives, benzyl derivatives, and acetophenone derivatives, and oil-soluble organic peroxides such as oil-soluble ketone peroxide, peroxyketal, hydroperoxide, dialkyl peroxide, peroxy esters, and peroxycarbonate. These photopolymerization initiators may be commercially available products such as, for example, products from Ciba Specialty Chemicals sold under the trademark designations of Irgacure 184 (hydroxycyclohexyl-phenyl ketone) and Irgacure 2959 (1-[4-(2-hydroxyethoxy)-phenyl]-2-hydroxy-2-methyl-1-propan-1-on).

When an additional initiator is to be used in combination in this invention, the amount of the other initiator to be used is in the range of from 0 to 20 parts by weight, preferably from 0 to 15 parts by weight, and particularly preferably from 0 to 10 parts by weight, based on 100 parts by weight of the water absorbent resin. This rate corresponds to a smaller amount than the radical polymerization initiator such as, for example, not more than ½, further not more than ¹/₁₀, and particularly not more than ¹/₅₀ of the weight ratio of the water-soluble radical polymerization initiator. When a water-soluble radical polymerization initiator and/or a heat-degradable radical polymerization initiator are to be used in combination, the amount of the radical polymerization initiator is referred to a total amount thereof.

While the mixing of the radical polymerization initiator and the water absorbent resin mentioned above may be accomplished by mixing the radical polymerization initiator with the unmodified water absorbent resin, it is preferably performed by dissolving the initiator in an aqueous solution and then mixing the resultant aqueous solution with the water absorbent resin. Since the water absorbent resin is capable of absorbing water, the radical polymerization initiator can be uniformly dispersed on the surface of the water absorbent resin and uniformly mixed with the water absorbent resin by mixing the radical polymerization initiator in an aqueous solution form. The aqueous solution may contain, besides water, some other solvent in an amount which does not impair solubility of the radical polymerization initiator.

Further, when a radical polymerization initiator is added in a form of an aqueous solution, the amount of water in an aqueous solution used is not limited. In this connection, a form of mixing water into a water absorbent resin is not limited to a case where mixing is conducted in a form of an aqueous solution containing a radical polymerization initiator. After mixing a radical polymerization initiator and a water absorbent resin, water or an aqueous solution may be mixed therewith. Therefore, a hydrogel-like cross-linked product is obtained by polymerizing a monomer component, drying to give a water content of 0 to 50% by weight, and then directly mixing with a radical polymerization initiator, to obtain a water absorbent resin composition.

For improving the mixing property of the aqueous solution with a water absorbent resin composition, a mixing aid may be added to the water absorbent resin composition. Although the time of adding a mixing aid is not particularly critical, the mixing aid is preferably added at the same time as or prior to the mixing step (i).

The mixing aid is not particularly limited, as long as it is a water-soluble or water-dispersible compound except an ethylenically unsaturated monomer or a radical polymerization initiator, and it can repress the agglomeration of the water absorbent resin with water and improve the mixing of the aqueous solution with the water absorbent resin. The mixing aid is preferably a water-soluble or water-dispersible compound. As such a water-soluble or water-dispersible compound, surfactants, water-soluble polymers, hydrophilic organic solvents, water-soluble inorganic compounds, inorganic acids, inorganic acid salts, organic acids, and organic acid salts can be typically used. In this specification, the term "water-soluble compound" is referred to as a compound having solubility in 100 g of water at room temperature of not less than 1 g, preferably not less than 10 g. Since the addition of the mixing aid can repress the agglomeration of the water absorbent resin with water and induce the uniform mixing of the aqueous solution with the water absorbent resin, the active energy rays, in the subsequent step, can be radiated equally and evenly to the water absorbent resin and thus the uniform surface cross-linking of the entire water absorbent resin can be attained.

When a mixing aid is to be used, the form of the mixing aid is not particularly limited, and it may be used in a powdery form, or may be dissolved, dispersed, or suspended in a solution. Preferably, it is used in the form of an aqueous solution.

Further, in the case of using a mixing aid, the order of the addition of the mixing aid is also not particularly limited. Any method such as a method which comprises adding a mixing aid to a water absorbent resin, and then adding and mixing water and a radical polymerization initiator (in some cases, an aqueous solution containing them) to the mixture, and a method which comprises dissolving a mixing aid in an aqueous solution, and simultaneously mixing the resultant solution with a water absorbent resin can be used.

As the surfactant to be used herein, at least one kind of surfactant which is selected from the group consisting of nonionic surfactants and anionic surfactants having an HLB of not less than 7 may be adopted. Typical examples of such surfactants are sorbitan aliphatic esters, polyoxyethylene sorbitan aliphatic esters, polyglycerin aliphatic esters, polyoxyethylene alkyl ethers, polyoxyethylene alkylphenol ethers, polyoxyethylene acyl esters, sucrose aliphatic esters, higher alcohol sulfuric esters, alkyl naphthalene sulfonates, alkylpolyoxyethylene sulfate, and dialkyl sulfosuccinates. Among these surfactants, polyoxyethylene alkyl ethers can be preferably used. The number average molecular weight of the polyoxyethylene alkyl ether is preferably in the range of 200 to 100,000, more preferably 500 to 10,000. If the number average molecular weight is too large, the solubility in water may decrease and thus the mixing with the water absorbent resin may become inefficient because the concentration of the surfactant in the solution can not be increased. Also, the viscosity of the solution may be increased. Conversely, if the number average molecular weight is too small, the surfactant may become less effective as a mixing aid.

Typical examples of the water-soluble polymer are polyvinyl alcohol, polyethylne oxide, polyethylene glycol, polypropylene glycol, polyacrylamide, polyacrylic acid, sodium polyacrylate, polyethylene imine, methyl cellulose, carboxymethyl cellulose, hydroxyethyl cellulose, hydroxypropyl cellulose, dextrin, sodium alginate, and starch. Among these polymers, polyethylene glycol can be preferably used. The number average molecular weight of the polyethylene glycol, like polyoxyethylene alkyl ether, is preferably in the range of 200 to 100,000, more preferably 500 to 10,000.

Typical examples of the hydrophilic organic solvent are alcohols such as methyl alcohol, ethyl alcohol, propyl alcohol, isopropyl alcohol, butyl alcohol, isobutyl alcohol, and t-butyl alcohol; ketones such as acetone and methylethyl ketone; ethers such as dioxane, alkoxy(poly)ethylene glycol, and tetrahydrofuran; amides such as ε-caprolactam and N,N-dimethyl formamide; sulfxides such as dimethyl sulfoxide; and polyhydric alcohols such as ethylene glycol, diethylene glycol, propylene glycol, triethylene glycol, tetraethylene glycol, 1,3-propane diol, dipropylene glycol, 2,2,4-trimethyl-1,3-pentane diol, glycerin, 2-butene-1,4-diol, 1,3-butane diol, 1,4-butane diol, 1,5-pentane diol, 1,6-hexane diol, 1,2-cyclohexane dimethanol, 1,2-cyclohexanol, trimethylol propane, diethanol amine, triethanol amine, polyoxypropylene, pentaerythritol, and sorbitol. These hydrophilic organic solvents may be used either singly or in the form of a mixture of two or more members.

Typical examples of the water-soluble inorganic compound are alkali metal salts such as sodium chloride, sodium hydrogen sulfate, and sodium sulfate, ammonium salts such as ammonium chloride, ammonium hydrogen sulfate, and ammonium sulfate, alkali metal hydroxides such as sodium hydroxide and potassium hydroxide, polyvalent metal salts such as aluminium chloride, polyaluminium chloride, aluminium sulfate, potassium alum, calcium chloride, alkoxy titanium, zirconium ammonium carbonate, zirconium acetate, and non-reducible alkali metal salt pH buffer agents such as hydrogencarbonate, dihydrogen phosphate, and monohydrogen phosphate.

Further, typical examples of the inorganic acid (salt) are hydrochloric acid, sulfuric acid, phosphoric acid, carbonic acid, and boric acid, and the salts thereof, for example, alkali metal salts thereof, and alkali earth metal salts thereof may be cited. As typical examples of the organic acid (salt), acetic acid, propionic acid, lactic acid, citric acid, succinic acid, malic acid, and tartaric acid, and the salts thereof, for example, alkali metal salts thereof, and alkali earth metal salts thereof.

Among the compounds cited above, at least one water-soluble or water-dispersible compound selected from the group consisting of polyoxyethylene alkyl ethers, polyethylene glycol, water-soluble polyvalent metals, sodium chloride, ammonium hydrogen sulfate, ammonium sulfate, sulfuric acid, and hydrochloric acid may be preferably used as the mixing aid.

These mixing aids can be used singly or in the mixed form of two or more members. The amount of the mixing aid to be added is not particularly limited as long as it can repress the aggregation of the water absorbent resin with water, and improves the mixing of the aqueous solution with the water absorbent resin, as mentioned above. Typically, the mixing aid is preferably added in an amount in the range of from 0.01 to 40 parts by weight, more preferably from 0.1 to 5 parts by weight, to 100 parts by weight of the water absorbent resin.

In the step (i) according to this invention, the conditions for mixing a water absorbent resin, water, and a radical polymerization initiator, and optionally a mixing aid are not critical. For example, the mixing temperature in the step (i) is preferably in the range of from 0 to 150° C., or from 10 to 120° C., or from 20 to 100° C., or from 30 to 90° C., or from 40 to 70° C., in this order. If the mixing temperature exceeds 150° C., the water absorbent resin may be degraded by heat, and the surface water content of the water absorbent resin in the step (ii) may be too low due to evaporation of water and the like. Conversely, if the mixing temperature is less than 0° C., water would be condensed, thereby inhibiting the stable operation. Carrying out the mixing step at an elevated temperature is preferred because a radical polymerization initiator can act also with small radiation amounts due to the heat. Accordingly, in such a case, a mixing/irradiation system may be preferably closed so as to repress excessive leakage of steam and to increase a surface water content of a water absorbent resin in the step (ii) to a level of not less than 3.0% by weight. The temperatures of water absorbent resin and water prior to the step (i) are not also particularly limited. For example, the temperature of water absorbent resin prior to the step (i) is preferably in the range of from 0 to 150° C., or from 10 to 120° C., or from 20 to 100° C., or from 50 to 100° C., in this order. If the temperature of water absorbent resin prior to the step (i) exceeds 150° C., the water absorbent resin may be degraded by heat. Conversely, if the mixing temperature is less than 0° C., water may be condensed, thereby inhibiting a stable operation. The temperature of water prior to the step (i) is preferably in the range of from 5 to 80° C., more preferably from 10 to 60° C., particularly preferably from 20 to 50° C. If the temperature of water prior to the step (i) exceeds 80° C., excessive amounts of water may evaporate prior to the mixing step (i) and thus a sufficient amount of water can not be mixed with a water absorbent resin resulting in a surface water content of the water absorbent resin which is too low. Conversely, if it is less than 5° C., water may be condensed, thereby inhibiting stable operation. Further, the mixing time in the step (i) is not also particularly limited as long as the above components can be mixed uniformly. Typically, the mixing time is preferably in the range of from 0.1 second to 60 minutes, more preferably from 1 second to 30 minutes, further more preferably from 2 seconds to 20 minutes, most preferably from 5 seconds to 10 minutes. If the mixing time is less than the lower limit, water absorbent resin, water, and a radical polymerization initiator, and optionally a mixing aid may not be mixed uniformly. Conversely, if the mixing time exceeds the upper limit and becomes unduly long, an excess amount of water would penetrate into an inner part of the water absorbent resin, thereby unduly decreasing the water content on the surface.

Suitable devices for mixing a water absorbent resin, water, and a radical polymerization initiator are, for example, V-shape mixer, ribbon type mixer, screw type mixer, rotary circular plate type mixer, air-current type mixer, batch kneader, continuous kneader, paddle type mixer, or space type mixer.

(c) Active Energy Rays

It is known that in production of a water absorbent resin, the rate of polymerization can be increased upon exposure to active energy rays. For example, by adding a polymerizable monomer component, an internal cross-linking agent and a photopolymerization initiator and irradiating the resultant mixture with active energy rays such as ultraviolet rays, electron radiation, or γ rays, a water-insoluble absorbent resin having internal cross-links can be prepared. Then, as a method for cross-linking the surface of the water absorbent resin, the formation of surface cross-links can be achieved by using a surface cross-linking agent and promoting the relevant reaction by application of heat. For the surface cross-linking of the water absorbent resin, compounds such as polyhydric alcohols, polyvalent glycidyl ethers, haloepoxy compounds, and polyvalent aldehydes which contain a plurality of functional groups in one molecular unit may be used. Generally, by heating at from 100 to 300° C., these functional groups can react with carboxyl groups present on the surface of the water absorbent resin to give rise to a cross-linked structure on the surface of the water absorbent resin. In this invention, however, a cross-linked structure can be formed on a surface of a water absorbent resin by combining a radical polymerization initiator and exposure with active energy rays without requiring the presence of a surface cross-linking agent and a polymerizable monomer. By the method of this invention, absorbency against pressure (AAP) and the saline flow conductivity (SFC) of the modified water absorbent resin can be improved.

According to the method of this invention, a surface water content of a water absorbent resin in the water absorbent resin composition is controlled to be above a predetermined value when irradiated with active energy rays.

Specifically, in the irradiating step, a surface water content of the water absorbent resin in the water absorbent resin composition is controlled to be not lower than 3.0% by weight. The surface water content may be controlled to a level of not lower than 3.0% by weight at any point of time in the irradiating step, and it is not necessary to control to a level of not lower than 3.0% by weight throughout the course from the beginning to the end of the irradiating step. When a surface water content of the water absorbent resin is controlled to a level of not lower than 3.0% by weight throughout the course from the beginning to the end of the irradiating step, the modification (for example, introduction of a cross-linking structure) of a surface of the water absorbent resin may not be carried out efficiently conducted.

As described above, the surface water content may be controlled to a level of not lower than 3.0% by weight at least at any point of time in the irradiating step. It is preferably controlled to a level of not lower than 3.5% by weight, and more preferably not lower than 4.0% by weight. The upper limit of the surface water content is not particularly critical, and it may be appropriately selected in accordance with purposes. However, the surface water content is typically not higher than 60.0% by weight, preferably not higher than 50.0% by weight, more preferably not higher than 40.0% by weight, and further preferably not higher than 30.0% by weight. When the surface water content is too high, water absorbent resin particles may adhere or agglomerate, and irradiation with active energy rays may not be effectively carried out.

In a typical embodiment of the present invention, the surface water content at the beginning of the irradiating step is controlled so as to be within the above-described range. It should be noted that during the irradiating step, the surface water content may be varied. Namely, the surface water content may be increased or decreased as compared to the initial water content. However, the surface water content should be within the above-described range. The surface water content is controlled to be within the above-described range, in preferably not lower than 30%, more preferably not lower than 60%, further preferably not lower than 90%, and particularly preferably 100% (that is, the whole period), of the whole period of the irradiating step.

In this invention, the term "surface water content" is referred to a weight percentage of a water amount existing in the vicinity of a surface of a particle based on a weight of a water absorbent resin particle. It is essentially different from a concept of a water amount or the water content in the whole particle. The surface water content is measured by the method specified in the working example cited below. The measuring method is briefly explained, as follows. Water is extracted by adding a hydrophilic organic solvent to the water absorbent resin composition obtained in the step (i), a water amount in the extract is quantitatively determined by Karl Fischer method, and thus a value of the surface water content can be calculated.

In the irradiating step, the method of controlling a surface water content of a water absorbent resin is not especially limited. For example, to attain a preferable surface water content a sufficient amount of water can be added into a water absorbent resin composition obtained in the step (i), or permeation of water into an inner part of a water absorbent resin particle can be promoted; or water evaporation into the atmosphere can be suppressed in the mixing step (i) and in the irradiating step (ii). Since an extent of permeation of water into an inner part of a water absorbent resin particle is influenced by time and temperature, it is preferable to control the temperature in a system during the mixing step (i). Further, to suppress evaporation of water, it is preferable have a closed system, to control the mixing time and the temperature in the system. In the irradiating step (ii), when a stirring apparatus having a box-like or a cylinder-like shape, for instance, a closed system can be obtained by covering an opening part for irradiation with a material capable of transmitting active energy rays, such as quartz glass. Promoting permeation of water to an inner part of a water absorbent resin can be achieved by extending the mixing step (i); or by putting the water absorbent resin composition in a closed system: or by heat treating the water absorbent resin composition at a temperature of not higher than a boiling point of water. On the other hand, promoting diffusion of water from a surface can be achieved by subjecting an air stream to a water absorbent resin composition; or by putting the water absorbent resin composition in an open system: or by heat treating the water absorbent resin composition at a temperature of not lower than a boiling point of water.

To monitor the a surface water content, the water absorbent resin composition may be dried to a certain range, or a predetermined amount of water may be added to a water absorbent resin composition, depending on the monitored value. Moreover, when water is added, penetration and diffusion of water from a surface to an inner part of the water absorbent resin may appropriately be controlled, or evaporation of water from a surface of a water absorbent resin may appropriately be controlled.

In this invention, the irradiation with active energy rays may be conducted while water absorbent resin, water and radical polymerization initiator are mixed, or the irradiation may be conducted after mixing at least two of these.

As typical examples of active energy rays, ultraviolet rays, electron radiation, and γ rays may be cited. These active energy rays may be used either singly or in the form of a combination of two or more members. Among these active energy rays, ultraviolet rays and electron radiation prove advantageous. In consideration of influence of active energy rays on human body, ultraviolet rays are more preferable and ultraviolet rays having a wavelength not exceeding 300 nm and particularly preferably in the range of 180-290 nm are particularly preferable.

As regards irradiating conditions, when the ultraviolet rays are used, intensity of irradiation is preferably in the range of 3-1,000 mW/cm$^2$, and dose of irradiation is preferably in the range of 100-10,000 mJ/cm$^2$. Typical examples of the device for irradiation with ultraviolet rays are high-pressure mercury-vapor lamp, low-pressure mercury-vapor lamp, metal halide lamps, xenon lamp, and halogen lamps. As long as ultraviolet rays, preferably ultraviolet rays of a wavelength of not more than 300 nm, are used, the use of additional different radiation types or different wavelengths is not particularly restricted. If electron radiation is used, voltage of acceleration is preferably in the range of 50-800 kV and absorbed dose is preferably in the range of 0.1-100 Mrad.

Generally, the duration of irradiating with active energy rays is preferably not less than 0.1 minute and less than 60 minutes, more preferably not less than 0.2 minute and less than 30 minutes, and more preferably not less than 1 minute and less than 15 minutes. Contrary thereto, conventional surface cross-linking using a conventional surface cross-linking agent, typically requires more time. For surface cross-linking by irradiation with active energy rays, no application of heat is required. The irradiation of active energy rays, however, possibly results in generation of radiant heat. Generally, a water absorbent resin can be treated at a temperature preferably less than 150° C., more preferably less than 120° C., still more preferably in the range of room temperature to 100° C., and particularly preferably in the range of 50-100° C. Thus, this invention allows a treating temperature below the typical temperature of conventional surface cross-linking.

Throughout irradiation with active energy rays, the water absorbent resin is preferably stirred or otherwise agitated to ensure uniform irradiation with the active energy rays. Typical examples of stirring devices are shaking mixer, shaking feeder, ribbon type mixer, conical ribbon type mixer, screw type mixing extruder, air current type mixer, batch kneader, continuous kneader, paddle type mixer, high-speed fluidifying mixer, and buoyant fluidifying mixer.

Further, irradiation may originate from the surrounding of an apparatus, while the water absorbent resin composition is in an apparatus having a form of a box or a cylinder. In this case, to make the mixture flow, a pressure of gas such as air or the like may be utilized, as is used in flowing a powder with air. When air is used, it is preferable to humidify the air to prevent the water absorbent resin composition from drying. When irradiation with active energy rays is conducted from many directions, subsequently or, preferably simultaneously, uniform surface treatment can be conducted in a short period. In this connection, the material of which the above-described apparatus is made is not particularly critical, as long as it does not obstruct irradiation with active energy rays onto the water absorbent resin composition. For example, quartz glass would be a suitable material.

(d) Other Treatment

After irradiation with active energy rays, the water absorbent resin may optionally be subjected to heat treatment at a temperature in the range of 50-250° C. for drying.

Further, after the irradiation with active energy rays, a water absorbent resin may be further surface cross-linked by using a conventional surface cross-linking agent such as polyhydric alcohols, polyvalent epoxy compounds, and alkylene carbonates.

In the method for producing a modified water absorbent resin of the present invention, a water absorbent resin may be added with an agent for enhancing liquid-permeability before, after or during irradiation with active energy rays. Typical examples of such an agent are minerals such as talc, kaolin, fuller's earth, bentonite, activated clay, barite, natural asphaltum, strontium ore, ilmenite, and pearlite; aluminum compounds such as aluminum sulfates 14-18 hydrates (or anhydrides), potassium aluminum sulfates 12 hydrate, sodium aluminum sulfate 12 hydrate, aluminum chloride, aluminum polychloride, and aluminum oxide, and aqueous solutions thereof; other polyvalent metal salts; hydrophilic amorphous silica (such as, for example, a product by dry method made by Tokuyama K.K. and sold under the trademark designation of "Reolosil QS-20" and products by precipitation method made by DEGUSSA Corp. and sold under the trademark designation of "Sipemat 22S" and "Sipernat 2200"); and oxide composites such as silicon oxide-aluminum oxide-magnesium oxide composite (such as, for example, a product made by ENGELHARD Corp. and sold under the trademark designation of "Attagel #50"), silicon oxide-aluminum oxide composite, and silicon oxide-magnesium oxide composite. The amount of such a liquid-permeability enhancing agent would preferably be in the range of from 0 to 20 parts by weight, more preferably from 0.01 to 10 parts by weight, and particularly preferably from 0.1 to 5 parts by weight with 100 parts by weight of a water absorbent resin which has been modified. The liquid-permeability enhancing agent can be added in the form of an aqueous solution if it is water-soluble or in the form of powder or slurry when it is water-insoluble. The liquid-permeability enhancing agent may also be added in a mixed form with a radical polymerization initiator. Other additives such as antibacterial agent, deodorant, and chelating agent may additionally be used in an amount in the range as mentioned above for the liquid-permeability enhancing agent.

(e) Modified Water Absorbent Resin

According to the method for producing a modified water absorbent resin of this invention, the produced water absorbent resin has improved absorbency against pressure. It has been hitherto known that the formation of surface cross-linking results in slightly lowering the free swelling capacity while increasing the ability to retain absorbed liquid even under pressed state, namely absorbency against pressure (AAP). By the method of this invention, the absorbency against pressure of 4.83 kPa of the water absorbent resin can be improved by not less than 1 g/g comparing with the absorption against pressure of the resin prior to the modification. It is believed that an increase in AAP indicates that surface cross-linking has taken place. The increase in the absorbency against pressure after the modification is preferably not less than 8 g/g, more preferably not less than 12 g/g, still more preferably not less than 15 g/g, and particularly preferably not less than 20 g/g, most preferably not less than 22 g/g. The modified water absorbent resin of this invention may exhibit absorbency against pressure of 4.83 kPa in the range of 8-40 g/g.

The centrifuge retention capacity (CRC) of the modified water absorbent resin is preferably not more than 50 g/g, more preferably not more than 40 g/g, still more preferably not more than 35 g/g. Although the lower limit thereof is not particularly limited, it is preferably not less than 10 g/g, more preferably not less than 20 g/g, still more preferably not less than 25 g/g. If the centrifuge retention capacity (CRC) exceeds 50 g/g, gel strength might be decreased, decreasing absorbency against pressure. On the hand, if the centrifuge retention capacity (CRC) is less than 10 g/g, sufficient water absorption capacity may not be obtained.

The modified water absorbent resin which is obtained by this invention has a saline flow conductivity (SFC) preferably of not less than 10 ($\times 10^{-7} \cdot cm^3 \cdot s \cdot g^{-1}$), more preferably not less than 30 ($\times 10^{-7} \cdot cm^3 \cdot s \cdot g^{-1}$), and still more preferably not less than 50 ($\times 10^{-7} \cdot cm^3 \cdot s \cdot g^{-1}$), particularly preferably not less than 70 ($\times 10^{-7} \cdot cm^3 \cdot s \cdot g^{-1}$), most preferably not less than 100 ($\times 10^{-7} \cdot cm^3 \cdot s \cdot g^{-1}$). The value is to be determined by the method specified in the working example cited herein below.

Further, the modified water absorbent resin which is obtained by this invention has low residual monomer content. It is believed that this is due to a reaction between the remaining monomers in the water absorbent resin with the initiator radicals formed by irradiation on a radical polymerization initiator with active energy rays. Since the water absorbent resin is used in hygienic materials such as disposable diaper, the residual monomer content is preferably as small as possible in terms of odor and safety. While a residual monomer content of water absorbent resin as a base polymer is generally in the range of 200 to 500 ppm, the residual monomer content of the water absorbent resin surface-treated by this invention is typically not more than 200 ppm (the lower limit is 0 ppm). The residual monomer content of the modified water absorbent resin is preferably not more than 200 ppm, more preferably not more than 150 ppm, particularly not more than 100 ppm (the lower limit is 0 ppm).

Further, the modified water absorbent resin which is obtained by this invention has a smaller solid content as compared with a modified water absorbent resin obtained by conventional surface cross-linking. This is because according to the method of this invention, the reaction does not require an elevated temperature and thus the water contained in the aqueous solution which is added to a water absorbent resin does not evaporate or only to a small degree Due to the large water content of the water absorbent resin, there is only a small amount of fine powder having a particle size of not more than 150 μm. Such particles are not desirable in terms of health. Also, the generation of static electricity on particle surface which causes blocking during the pneumatic conveying can be prevented, and the degradation of physical properties by physical damage during the pneumatic conveying can be repressed. The solid content of the modified water absorbent resin is preferably not more than 95%, more preferably not more than 93%, particularly not more than 91%. Although the lower limit is not critical, a solid content of not more than 70% may lead to decreased absorbency per weight of the water absorbent resin.

The properties of the surface-treated water absorbent resin which is obtained by this invention can be further adjusted by treatment conditions such as by selecting a suitable unmodified water absorbent resin and agglomeration and molding processes of a water absorbent resin after surface cross-linking. Generally, the modified water absorbent resin is in a powdery form. This powder has a weight average particle diameter (specified by classification with sieves) in the range of from 10 to 1,000 μm, and preferably from 200 to 600 μm. In this powder, the content of particles having diameters of from 150 to 850 μm is preferably in the range of from 90 to 100% by weight, and more preferably from 95 to 100% by weight, based on the weight of the water absorbent resin.

The method of this invention effects an agglomerating a fine powder generated in the production of a water absorbent resin during the course of surface cross-linking of the water absorbent resin. Accordingly, even if the water absorbent resin prior to the modification happens to contain a fine powder, the method for producing a modified water absorbent resin of this invention permits the agglomeration of the contained fine powder, which can lead to an decreased amount of fine powder in the resultant modified water absorbent resin. Thus, the particle size distribution of the produced modified water absorbent resin is shifted toward a larger particle size as compared with the water absorbent resin prior to the modification. The degree of the shift, however, may vary and depends, for example, on the amount of a radical polymerization initiator mixed with the water absorbent resin, on the water content, on the conditions of irradiation with active energy rays, and on the flowing process during the irradiation.

The modified water absorbent resin which is obtained by the method of this invention has surface cross-links formed uniformly and with a high cross-link density throughout the entire surface of the water absorbent resin. Thereby good characteristics, such as absorption capacity, absorption speed, gel strength, and suction power which a water absorbent resin can be obtained. Conventionally, speed and extent of the surface cross-linking have been found to depend on the ratio of neutralization, when an acrylic acid type water absorbent resin is subjected to surface cross-linking by using such a surface cross-linking agent as polyhydric alcohol, polyvalent epoxy compound, or alkylene carbonate. Specifically, the surface cross-linking proceeds fast when the ratio of neutralization is low, while surface cross-linking proceeds with difficulties when the ratio of neutralization is high. For the purpose of surface cross-linking the water absorbent resin to be obtained by the post-neutralization of polyacrylic acid, post-neutralization had to be performed uniformly after surface cross-linking. Contrary thereto, according to this invention, surface cross-linking of the water absorbent resin can be done independently from the ratio of neutralization of a water absorbent resin and independently from uniformity of post-neutralization. It is believed that since surface cross-linking depends on the action of a radical polymerization initiator on a main chain of the water absorbent resin, surface cross-linking can proceed regardless of whether a carboxyl group is present in the form of an acid or a salt.

If this invention is executed in the presence of an ethylenically unsaturated monomer, the radical polymerization initiator is consumed by the polymerization of the ethylenically unsaturated monomer, which is not desirable in the present invention.

In accordance with this invention, surface treatment of the water absorbent resin can be carried out fully satisfactorily even at reaction temperatures near room temperature, and the surface-treated water absorbent resin consequently obtained has good characteristics, such as absorption capacity, absorption speed, gel strength, and suction power which the water absorbent resin. Accordingly, the water absorbent resin which is obtained by this invention is optimally suitable for use in absorbent members, such as disposable diapers, training pants, sanitary napkins and other sanitary materials for absorbing body fluid.

Absorbent Articles

The absorbent members made by the method of the present invention are preferably used as absorbent cores in absorbent articles. As used herein, absorbent article refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, diaper holders and liners, sanitary napkins and the like.

Preferred absorbent articles of the present invention are diapers and training pants. As used herein, "diaper" and "training pants" refers to an absorbent article generally worn by infants and incontinent persons about the lower torso.

Absorbent articles especially suitable for the present invention typically comprise an outer covering including a liquid pervious topsheet, a liquid impervious backsheet and an absorbent core generally disposed between the topsheet and the backsheet. The absorbent core may comprise any absorbent material that is generally compressible, conformable, non-irritating to the wearer's skin, and capable of absorbing and retaining liquids such as urine and other certain body exudates. In addition to the SAP particles of the present invention, the absorbent core may comprise a wide variety of liquid-absorbent materials commonly used in disposable diapers and other absorbent articles such as comminuted wood pulp, which is generally referred to as air felt.

Exemplary absorbent structures for use as the absorbent assemblies are described in U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From high In al. on Jul. 22, 1997.

EXAMPLES

In the following, this invention will be described more specifically by working examples and comparative examples. This invention is not limited thereto. Hereinafter, the "parts by weight" may be expressed simply as "parts" and the "liters" simply as "L" for the sake of convenience. The method of determination and the method of evaluation indicated in the working examples and the comparative example will be shown below.

(1) Particle Size Distribution: Weight Average Particle Diameter (D50) and Logarithmic Standard Deviation ($\sigma\xi$)

A water absorbent resin or particulate absorbent of 10 g is passed through JIS standard sieves having mesh sizes of 850 μm, 710 μm, 600 μm, 500 μm, 425 μm, 300 μm, 212 μm, 150 μm, 106 μm, and 45 μm (THE IIDA TESTING SIEVE, made by Iida Seisakusho K.K., 8 cm in diameter), at room temperature (20 to 25° C.) and at humidity of 50 RH %, and then classified by using a sieve shaker (IIDA SIEVE SHAKER, TYPE: ES-65type, SER. No. 0501, made by Iida Seisakusho K.K.) for 5 minutes. As for a weight average diameter, residual percentage R is plotted on a logarithmic probability paper, and from this plotting, a particle diameter corresponding to R=50 wt % reads as a weight average diameter (D50). Further, the particle diameters with R being 84.1% by weight and 15.9% by weight are referred to as X1 and X2, respectively. The logarithmic standard deviation ($\sigma\xi$) is represented by the following formula. Specifically, it means that the smaller the value $\sigma\xi$ is, the narrower the particle size distribution is.

$$\sigma\xi = 0.5 \times 1n(X2/X1)$$

(2) Surface Water Content 500 g of a water absorbent resin as a base polymer are added to 5 liters of Loedige mixer (made by Loedige Co., Ltd., Type: M5R), and a treating solution obtained prior to mixing 5.0 g of ammonium persulfate, 2.5 g of a monomethyl ether of a polyethylene glycol (a number average molecular weight of about 2,000) and 40 g of water, are sprayed thereto under stirring at 300 rpm. After being mixed by stirring for 3 min at room temperature, the stirring is terminated. The resultant mixture of 1 g is added to a screw tube, and 4 g of methanol anhydride is added. Then, the mixture is shaken for 30 seconds with a mini-shaker MS1 made by IKA K.K., and thereafter it is absorbed with a syringe, then is filtrated with a filter (made by Zeal Science Co., Ltd.; Water type 25 A (a pore diameter of 0.45 μm)). The amount of water contained in a filtrate is measured by a method below with a Karl Fischer moisture meter (made by Kyoto Electronics Manufacturing Co., Ltd.; Type: MKS-1S).

Measurement of Amount of Water with a Karl Fischer Moisture Meter

1. Principle for Measurement

This is a method of measuring an amount of water using a volumetric analysis, wherein a Karl Fischer reagent in which water reacts quantitatively with iodine and sulfurous acid gas in the presence of methyl alcohol and pyridine, is used as a titrant.

Polarization is conducted by making slight constant electric current between two platinum electrodes immersed in a solution, and an end point of titration is determined by a Dead Stop method wherein a potential change caused by excessive iodine at an end point is detected. To measure an amount of water by a Karl Fischer method, a sample is put in a flask for titration, titrated with a Karl Fischer reagent, and an amount of water in the sample is determined as a product of a titration amount of a Karl Fischer reagent and a titer.

$$W = K \times F$$

wherein W is an amount of water (mg) in a sample;
K is a titration amount of a Karl Fischer reagent (mL); and
F is a titer of a Karl Fischer reagent (mg/mL).

2. Measuring Method 50 mL of a solvent for measurement (a mixed product of 50 mL of an acetic acid (special grade), 50 mL of Buffer solution (HYDRNAL-Buffer), and 900 mL of methanol anhydride) is charged until electrodes in a Karl Fischer moisture meter are immersed therein. Then, titration is conducted with a Karl Fischer reagent by pushing a "START" key, to make an inner part of a flask for titration in an anhydrous state.

A sample is put into a flask for titration, titration is conducted with a Karl Fischer reagent by pushing a "START" key. A weight of the sample (a) [mg] and an amount of Karl Fischer titration (b) [mL] are recorded. Measuring was conducted by three times in all, and an average value is calculated.

By inserting the weight of the sample (a) and the amount of Karl Fischer titration (b) into the equation (1) below, the water content (c) [wt %] in methanol anhydride, which is used in extraction of water from a mixture containing a water absorbent resin, is calculated. As for F (titer of a Karl Fischer reagent), measuring is conducted by using HYDRNAL-Composite 5K (about 5 mg H$_2$O/mL), and it is calculated by inserting the value into the equation (2) below.

$$(c) = ((b) \times F/(a)) \times 100 \qquad (1)$$

$$F(mg/mL) = [\text{HYDRNAL-Composite } 5K \text{ (about 5 mg H}_2\text{O/mL)}] \times [\text{a solution amount of HYDRNAL-Composite } 5K \text{ [mL]}]/[\text{a titration amount of a Karl Fischer reagent [mL]}] \qquad (2)$$

The total (d) [wt %] water concentration contained in methanol anhydride is measured. The water concentration derived from water contained in the water absorbent resin before addition of the treating agent is subtracted from the water concentration (c) in methanol anhydride which is used in extraction of water from the mixture containing the water absorbent resin mixture as calculated in the above described equation (1). Thereby, concentration (e), namely (c)−(d)=(e) is obtained. The amount of water (g) [mg] which is extracted from the water absorbent resin mixture is calculated by using the concentration (e) and an amount of methanol anhydride (f) [mg] to be used in extraction of water from the water absorbent resin mixture, in accordance with the following equation (3).

$$(g)=((c)-(d))\times(f)=(e)\times(f) \quad (3)$$

Further, the amount of water (h) [mg] derived from the treating solution, which is contained in a water absorbent resin mixture (a), can be calculated by using the following equation (4), based on the weight (i) [mg] of the treating solution added per 1,000 mg of the water absorbent resin and the weight of water (j) [mg] contained in the treating solution.

$$(h)=(a)\times(j)/(1000+(i)) \quad (4)$$

The ratio of water (g) extracted from the water absorbent resin to water (h) derived from the treating solution, which is contained in a water absorbent resin mixture (a), is calculated from the following equation (5), which is made as an extraction ratio (k) [wt %].

$$(k)=((g)/(h))\times 100 \quad (5)$$

The weight ratio (l) [wt %] of the amount of water contained in a treating solution added to the water absorbent resin multiplied with the amount of the water absorbent resin and the extraction ratio (k) gives the surface water content (m) [wt %] according to the following equation (6):

$$(m)=(l)\times((k)/100) \quad (6)$$

(3) Centrifuge Retention Capacity (CRC)

CRC indicates absorbency in an aqueous 0.90 wt. % sodium chloride solution (hereinafter also called simply as "physiological saline") without load for 30 min. 0.200 g of a water absorbent resin is uniformly put in a pouch (85 mm×60 mm) made of a non-woven fabric (made by Nangoku Pulp Kogyo K.K., Product Name; Heatlon Paper, Model GSP-22), and heat-sealed. Then, the pouch is immersed at room temperature in large excess (about 500 mL) of physiological saline. After 30 min, the pouch is pulled out, and water is removed with a centrifuge (made by Kokusan Co., Ltd., Type: H-122) by centrifugal force (250 G) as described in "Edana ABSORBENCY II 441.1-99" for 3 min. Then, the weight of the pouch is measured, which is referred to as W1 (g). Further, the same is done without using the water absorbent resin, to measure the weight, which is referred to as W0 (g). From these values, W1 and W0, the CRC (g/g) is calculated according to the equation below.

$$CRC\ (g/g)=[(W1-W0)/\text{Weight of water absorbent resin}]-1$$

(4) Absorbency Against Pressure (AAP)

400-mesh wire gauze of stainless steel (38 μm in mesh size) is welded to a bottom of a plastic supporting cylinder having an inner diameter of 60 mm. At room temperature (25±2° C.) and 50 RH % of humidity, 0.900 g of a given water absorbent resin is uniformly scattered on the wire gauze. A piston and a load, each of which is adjusted to exert a load of 4.83 kPa uniformly on the water absorbent resin, has an outer diameter slightly smaller than 60 mm but produces no gap relative to the inner wall surface of the supporting cylinder, and does not have its unobstructed vertical motion prevented, were mounted thereon sequentially in the order mentioned, and the whole weight $W_a$ (g) of the resultant measuring device is determined.

A glass filter 90 mm in diameter (pore diameter: 100 to 120 μm: made by Sogo Rikagaku Glass Manufactory K.K.) is placed inside a petri dish 150 mm in diameter. An aqueous 0.9 wt. % sodium chloride solution (physiological saline) (20-25° C.) is added to the petri dish so as to give the same level as the upper surface of the glass filter. One filter paper 90 mm in diameter (0.26 mm in thickness and 5 μm in retained particle diameter; made by Advantec Toyo K.K. and sold under the product name of "JIS P 3801, No. 2") is mounted on the surface of physiological saline so as to have the surface thereof thoroughly wetted and the excess solution is removed.

The resultant measuring device is wholly mounted on the wetted filter paper and the water absorbent resin is allowed to absorb the solution under load for a prescribed time of one hour. The whole measuring device is lifted after the one hour's standing, and the weight thereof $W_b$ (g) is determined. This determination of the weight must be performed as quickly as possible without exposing the device to any vibration. The absorbency against pressure (AAP) (g/g) is calculated in accordance with the following formula using $W_a$ and $W_b$.

$$AAP\ (g/g)=[W_b(g)-W_a(g)]/\text{Weight of water absorbent resin (g)}$$

(5) Total Water Content

In an aluminum cup having a bottom with a diameter of 4 cm and a height of 2 cm, 1.00 g of a water absorbent resin is spread uniformly on the bottom. The aluminum cup containing the water absorbent resin is weighed [W4 (g)]. The cup is left in a hot air drier kept at 180° C. for 3 hours. Immediately (within at least 1 minute) after the cup is taken out of the hot air drier, the aluminum cup containing the water absorbent resin is weighed [W5 (g)]. The total water content is calculated from the values W4 and W5 by the following formula.

$$\text{Total water content (\% by weight)}=[(W4(g)-W5(g))/(\text{Weight of water absorbent resin (g)})]\times 100$$

(6) Saline Flow Conductivity (SFC)

SFC is a value which indicates the degree of liquid permeability exhibited by water absorbent resin particles in a swollen state. A larger SFC value indicates higher liquid permeability.

The SFC is determined in accordance with the test for the saline flow conductivity (SFC) described in JP-T-9 (1997)-509591 with necessary modification.

Specifically, by the use of a device illustrated in FIG. 1, SFC is determined. In the device illustrated in FIG. 1, a tank 31 has a glass tube 32 inserted therein and the lower end of the glass tube 32 is disposed so that an aqueous 0.69 wt. % sodium chloride solution 33 can be maintained to a height of 5 cm from the bottom of the swelled gel 44 held in a cell 41. The aqueous 0.69 wt. % sodium chloride solution in the tank 31 is supplied to the cell 41 via an L-letter tube 34 fitted with a cock. Below the cell 41, a container 48 for collecting the passed liquid is disposed and the collecting container 48 is set on a pan scale 49. The cell 41 has an inside diameter of 6 cm. A wire gauze (opening of sieve: 38 μm) 42 of stainless steel of No. 400 is disposed on the bottom surface in the lower part of the cell. A piston 46 is provided in the lower part thereof with holes 47 sufficient for passing a liquid, and fitted in the bottom part thereof with a glass filter 45 having good permeability so as to prevent the water absorbent resin or the swelled gel thereof from entering the hole 47. The cell 41 is laid on a stand for mounting the cell. The surface of the stand contacting the cell is placed on a wire gauze 43 of stainless steel incapable of obstructing the passage of liquid.

Artificial urine is prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of diammonium hydrogen phosphate, and 994.25 g of purified water together.

Water absorbent resin (0.900 g) is uniformly placed in a container 40 and left swelling with an artificial urine under a pressure of 0.3 psi (2.07 kPa) for 60 minutes, and a height of a gel layer of gel 44 is recorded. Subsequently, under a pressure of 0.3 psi (2.07 kPa), an aqueous 0.69 wt. % sodium chloride solution 33 from a tank 31 is passed under a stated hydrostatic pressure through the swelled gel layer. By means of a computer and a balance, the amounts of liquid passing through the gel layer at intervals of 20 seconds are recorded as a function of time over 10 minutes. A flow speed Fs (t) through the swelled gel 44 (mainly between adjacent particles) is determined in unit of [g/s] by dividing an increased weight (g) by an increased time (second). The time in which the constant hydrostatic pressure and the stable flow speed are attained is denoted as Ts. The data obtained for 10 minutes and Ts are exclusively used for the calculation of flow speed. The value Fs (t=0), namely an initial flow speed through the gel layer, is calculated by using the flow speed obtained over 10 minutes and Ts. Specifically, the Fs (t=0) is calculated by extrapolating the result of the least-squares method performed on the Fs (t) against time into t=0.

$$SFC = [Fs(t=0) \times L0] / (\rho \times A \times \Delta P)$$
$$= [Fs(t=0) \times L0] / 139506$$

wherein Fs (t) stands for a flow speed expressed in units of [g/s],

L0 stands for a height of a gel layer expressed in units of cm, $\rho$ stands for a density of an aqueous 0.69 wt. % sodium chloride solution (1.003 g/cm$^3$), A stands for an upper side area of a gel layer in a cell 41 (28.27 cm$^2$), $\Delta P$ stands for a hydrostatic pressure exerted on a gel layer (4920 dynes/cm$^2$), and a unit of SFC is ($10^{-7} \cdot cm^3 \cdot s \cdot g^{-1}$).

Production Example 1

In a reaction vessel which is formed from a jacketed, double-arm type kneader of stainless steel with an inner volume of 10 L and provided with two sigma-type blades, and a lid further attached thereto, 5,437 g of an aqueous solution of sodium acrylate (a monomer concentration: 39 wt. %) having a neutralization ratio of 60 mol % is placed. Then, 7.90 g of a polyethylene glycol diacrylate (a number of average ethylene oxide units: n=9) as an internal cross-linking agent is dissolved in the aqueous solution, to prepare a reaction solution. Further, the reaction solution is deaerated under a nitrogen atmosphere. Subsequently, 30.19 g of an aqueous 10 wt. % sodium persulfate solution as a polymerization initiator and 25.16 g of an aqueous 0.1 wt. % L-ascorbic acid solution are added to the reaction solution while stirring. As a result, polymerization begins after about one minute. While pulverizing the gel formed, polymerization is conducted at 20 to 95° C., and the hydrogel-like cross-linked polymer is taken out 30 minutes after the beginning of the polymerization. The particle diameter of the hydrogel-like cross-linked polymer obtained is not larger than 5 mm. The pulverized hydrogel-like cross-linked polymers are scattered on a wire mesh of 50 mesh (opening of sieve: 300 μm), and are dried in hot air at 175° C. for 50 minutes. Thus, easily pulverizable powdery agglomerates having an amorphous form are obtained.

The resultant powdery agglomerates are pulverized with a roll mill, and are further classified with a JIS standard sieve having an opening of sieve of 710 μm. Next, particles which passed through a sieve having an opening of sieve of 710 μm in the above-described operation, are classified with a JIS standard sieve having a opening of sieve of 150 μm, to remove particles which pass through a sieve having a opening of sieve of 150 μm. Thus, water absorbent resin (A) is obtained.

The particle distribution of the resultant water absorbent resin (A) is shown in Table 1 below, and various properties thereof are shown in Table 2 below.

Production Example 2

In a reaction vessel which is formed from a jacketed, double-arm type kneader of stainless steel with an inner volume of 10 L and provided with two sigma-type blades, and a lid further attached thereto, 5,443 g of an aqueous solution of sodium acrylate (a monomer concentration: 39 wt. %) having a neutralization ratio of 90 mol % is placed. Then, 6.11 g of a polyethylene glycol diacrylate (a number of average ethylene oxide units: n=9) as an internal cross-linking agent is dissolved into the aqueous solution, to prepare the reaction solution. Further, the reaction solution is deaerated under nitrogen atmosphere. Subsequently, 28.02 g of an aqueous 10 wt. % sodium persulfate solution as a polymerization initiator and 23.35 g of an aqueous 0.1 wt. % L-ascorbic acid solution are added to the reaction solution while stirring. As a result, polymerization begins after about one minute. While pulverizing the gel formed, polymerization is conducted at 20 to 95° C., and the hydrogel-like cross-linked polymer is taken out 30 minutes after the beginning of the polymerization. The particle diameter of the hydrogel-like cross-linked polymer obtained is not larger than 5 mm. The pulverized hydrogel-like cross-linked polymers are scattered on a wire mesh of 50 mesh (opening of sieve: 300 μm), and are dried in hot air at 175° C. for 50 minutes. Thus, easily pulverizable powdery agglomerates having an amorphous form are obtained.

The resultant powdery agglomerates are pulverized with a roll mill, and are further classified with a JIS standard sieve having an opening of sieve of 710 μm. Next, particles which passed through a sieve having an opening of sieve of 710 μm in the above-described operation, are classified with a JIS standard sieve having a opening of sieve of 150 μm, to remove particles which pass through a sieve having a opening of sieve of 150 μm. Thus, water absorbent resin (B) is obtained.

The particle distribution of the resultant water absorbent resin (B) is shown in Table 1 below, and various properties thereof are shown in Table 2 below. In Table 1, "not less than 850 μm" is referred to as the ratio (% by weight) of the water absorbent resin which remains on the sieve having a mesh size of 850 μm following the classification process. Also, "not more than 45 μm" is referred to as the ratio (% by weight) of the water absorbent resin which passes through a sieve having a mesh size of 45 μm following the classification process. Then, "x to y is referred to as the ratio (% by weight) of the water absorbent resin which passes through a sieve having a mesh size of x μm and also remains on a sieve having a mesh size of y μm following the classification process.

TABLE 1

|  | Production Example | |
|---|---|---|
|  | 1 | 2 |
| Water absorbent resin | A | B |
| D50 (μm) | 345 | 345 |
| σζ | 0.327 | 0.327 |
| Particle size distribution | | |
| not less than 850 μm (wt %) | 0.0 | 0.0 |
| 850 to 710 μm (wt %) | 0.1 | 0.1 |
| 710 to 600 μm (wt %) | 1.0 | 1.0 |
| 600 to 500 μm (wt %) | 3.7 | 3.7 |
| 500 to 425 μm (wt %) | 21.7 | 21.7 |
| 425 to 300 μm (wt %) | 39.6 | 39.6 |
| 300 to 212 μm (wt %) | 23.0 | 23.0 |
| 212 to 150 μm (wt %) | 9.3 | 9.3 |
| 150 to 45 μm (wt %) | 1.5 | 1.5 |
| not more than 45 μm (wt %) | 0.1 | 0.1 |
| Total (wt %) | 100.0 | 100.0 |

Example 1

500 g of the water absorbent resin (A) as a base polymer are added to 5 L of Loedige mixer (made by Loedige Co., Ltd., Type: M5R). A treating solution which had been prepared by mixing 12.5 g of ammonium persulfate, 2.5 g of polyethylene glycol monomethyl ether (a number average molecular weight of about 2,000) and 120 g of water, is sprayed under stirring at 300 rpm. After mixing is continued under stirring for additional 3 minutes at room temperature, to achieve permeation and diffusion of the added water into the inner part of particles, stirring is terminated once, and a sample charging port of a proshear mixer is taken out the surface water content of the water absorbent resin composition (1) thus obtained is 10.4% by weight.

After putting a glass plate made of quartz and having a thickness of 3 mm at opening part, stirring of the water absorbent resin composition (1) is restarted (a time necessary for restart was 30 seconds). A radiation device able to emit ultraviolet rays (made by Ushio Denki K.K., UV-152/IMNSC3-AA06) furnished with a metal halide lamp of 1 kW (made by the same company, UVL-1500M2-N1) is set at a distance of 8 cm between a center of the lamp and a quartz plate. Then, the water absorbent resin composition (1) is irradiated with ultraviolet rays at room temperature for 15 minutes, to obtain the modified water absorbent resin (1).

The thus obtained modified water absorbent resin (1) is tested for various properties, and the results are shown in Table 2 below. In the Table 2, "CRC after correction with total water content" and "AAP after correction with total water content" are calculated by the following formulas. In the following formulas, "CRC before correction with total water content" is referred to as a centrifuge retention capacity (CRC) of water absorbent resin prior to determination of total water content by the formula (5), and "AAP before correction with total water content" is referred to as an absorbency against pressure (AAP) of water absorbent resin prior to determination of total water content by the formula (5).

CRC after correction with total water content (g/g) = [(CRC before correction with total water content) (g/g) + 1]/(100 − Total water content of water absorbent resin)] × 100 − 1

AAP after correction with total water content (g/g) = AAP before correction with total water content (g/g)/(100 − Total water content of water absorbent resin)] × 100

Example 2

The same procedure as described Example 1 is repeated except that the water amount in the treating solution is changed to 160 g, to obtain water absorbent resin composition (2) having a surface water content of 12.5% by weight. Further, by the same procedure as described Example 1, the water absorbent resin composition (2) is irradiated with ultraviolet rays for 15 minutes, to obtain modified water absorbent resin (2).

The thus obtained modified water absorbent resin (2) is tested for various properties, and the results are shown in Table 2 below.

Example 3

The same procedure as described Example 1 is repeated except that the water amount in the treating solution is changed to 200 g, to obtain a water absorbent resin composition (3) having a surface water content of 15.5% by weight. Further, by the same procedure as described Example 1, the water absorbent resin composition (3) is irradiated with ultraviolet rays for 15 minutes, to obtain the modified water absorbent resin (3).

The thus obtained modified water absorbent resin (3) is tested for various properties, and the results are shown in Table 2 below.

Example 4

A water absorbent resin composition (4) having a surface water content of 12.5% by weight is obtained by repeating the same procedure as described Example 2. Further, by the same procedure as described Example 1, the water absorbent resin composition (4) is irradiated with ultraviolet rays for 1 minute, to obtain the modified water absorbent resin (4).

The thus obtained modified water absorbent resin (4) is tested for various properties, and the results are shown in Table 2 below.

Example 5

The same procedure as described Example 1 is repeated except that the water absorbent resin (B) is used as a base polymer instead, to obtain a water absorbent resin composition (5) having a surface water content of 6.5% by weight. Further, by the same procedure as described Example 1, the water absorbent resin composition (5) is irradiated with ultraviolet rays for 15 minutes, to obtain the modified water absorbent resin (5).

The thus obtained modified water absorbent resin (5) is tested for various properties, and the results are shown in Table 2 below.

Example 6

The same procedure as described Example 2 is repeated except that the water absorbent resin (B) is used as a base polymer instead, to obtain a water absorbent resin composition (6) having a surface water content of 6.7% by weight. Further, by the same procedure as described Example 1, the water absorbent resin composition (6) is irradiated with ultraviolet rays for 15 minutes, to obtain the modified water absorbent resin (6).

The thus obtained modified water absorbent resin (6) is tested for various properties, and the results are shown in Table 2 below.

Example 7

The same procedure as described Example 3 is repeated except that the water absorbent resin (B) is used as a base polymer instead, to obtain the water absorbent resin composition (7) having a surface water content of 9.6% by weight. Further, by the same procedure as described Example 1, the water absorbent resin composition (7) is irradiated with ultraviolet rays for 15 minutes, to obtain the modified water absorbent resin (7).

The thus obtained modified water absorbent resin (7) is tested for various properties, and the results are shown in Table 2 below.

Control 1

The same procedure as described Example 1 is repeated except that the water amount in the treating solution is changed to 20 g, to obtain a water absorbent resin composition for comparison (1) having a surface water content of 1.9% by weight. Further, by the same procedure as described Example 1, the water absorbent resin composition for comparison (1) is irradiated with ultraviolet rays for 15 minutes, to obtain the modified water absorbent resin for comparison (1).

The thus obtained modified water absorbent resin for comparison (1) is tested for various properties, and the results are shown in Table 2 below.

Control 2

The same procedure as described Example 1 is repeated except that the water amount in the treating solution is changed to 40 g, to obtain the water absorbent resin composition for comparison (2) having a surface water content of 4.5% by weight. Further, by the same procedure as described Example 1, the water absorbent resin composition for comparison (2) is irradiated with ultraviolet rays for 15 minutes, to obtain the modified water absorbent resin for comparison (2).

The thus obtained modified water absorbent resin for comparison (2) is tested for various properties, and the results are shown in Table 2 below.

Control 3

The same procedure as described Example 1 is repeated except that the water amount in the treating solution is changed to 80 g, to obtain the water absorbent resin composition for comparison (3) having a surface water content of 7.9% by weight. Further, by the same procedure as described Example 1, the water absorbent resin composition for comparison (3) is irradiated with ultraviolet rays for 15 minutes, to obtain the modified water absorbent resin for comparison (3).

The thus obtained modified water absorbent resin for comparison (3) is tested for various properties, and the results are shown in Table 2 below.

Control 4

A water absorbent resin composition for comparison (4) having a surface water content of 4.5% by weight is obtained by repeating the same procedure as described Control 2. Further, by the same procedure as described Example 4, the water absorbent resin composition for comparison (4) is irradiated with ultraviolet rays for 1 minute, to obtain the modified water absorbent resin for comparison (4).

The thus obtained modified water absorbent resin for comparison (4) is tested for various properties, and the results are shown in Table 2 below.

Control 5

The same procedure as described Control 1 is repeated except that the water absorbent resin (B) is used as a base polymer instead, to obtain the water absorbent resin composition for comparison (5) having a surface water content of 1.1% by weight. Further, by the same procedure as described Example 1, the water absorbent resin composition for comparison (5) is irradiated with ultraviolet rays for 15 minutes, to obtain the modified water absorbent resin for comparison (5).

The thus obtained modified water absorbent resin for comparison for comparison (5) is tested for various properties, and the results are shown in Table 2 below.

Control 6

The same procedure as described Control 3 is repeated except that the water absorbent resin (B) is used as a base polymer instead, to obtain the water absorbent resin composition for comparison (6) having a surface water content of 5.2% by weight. Further, by the same procedure as described Example 1, the water absorbent resin composition for comparison (6) is irradiated with ultraviolet rays for 15 minutes, to obtain the modified water absorbent resin for comparison (6).

The thus obtained modified water absorbent resin for comparison (6) is tested for various properties, and the results are shown in Table 2 below.

TABLE 2

| | | Composition of treating solution (wt. %)) | Mixing time of treating solution (min.) | Irradiation time of UV (min.) | Surface water content (wt. %) | Total water content (wt. %) | Total water content before correction | | Total water content after correction | | SFC ($10^{-7} \cdot cm^3 \cdot s \cdot g^{-1}$) |
|---|---|---|---|---|---|---|---|---|---|---|---|
| | | | | | | | CRC (g/g) | AAP (g/g) | CRC (g/g) | AAP (g/g) | |
| Production Ex. 1 | WAR (A) | — | — | — | 0.1 | 5.4 | 36.7 | 6.6 | 38.9 | 7.0 | 0 |
| Example 1 | WAR (1) | APS/PEG-OMe/W = 2.5/0.5/24 | 10 | 15 | 10.4 | 18.2 | 15.7 | 16.2 | 19.4 | 19.8 | 258 |
| Example 2 | WAR (2) | APS/PEG-OMe/W = 2.5/0.5/32 | 10 | 15 | 12.5 | 25.4 | 12.9 | 13.5 | 17.6 | 18.1 | 360 |
| Example 3 | WAR (3) | APS/PEG-OMe/W = 2.5/0.5/40 | 10 | 15 | 15.5 | 28.4 | 12.2 | 12.9 | 17.4 | 18.0 | 427 |
| Example 4 | WAR (4) | APS/PEG-OMe/W = 2.5/0.5/32 | 10 | 1 | 12.5 | 28.1 | 18.8 | 15.6 | 26.5 | 21.7 | 74 |
| Control 1 | WAR for com. (1) | APS/PEG-OMe/W = 2.5/0.5/4 | 10 | 15 | 1.9 | 8.6 | 28.7 | 21.8 | 31.5 | 23.9 | 15 |
| Control 2 | WAR for com. (2) | APS/PEG-OMe/W = 2.5/0.5/8 | 10 | 15 | 4.5 | 10.2 | 25.3 | 22.1 | 28.3 | 24.6 | 61 |
| Control 3 | WAR for com. (3) | APS/PEG-OMe/W = 2.5/0.5/16 | 10 | 15 | 7.9 | 15.2 | 18.9 | 18.2 | 22.5 | 21.5 | 159 |
| Control 4 | WAR for com. (4) | APS/PEG-OMe/W = 2.5/0.5/8 | 10 | 1 | 4.5 | 12.2 | 26.8 | 16.5 | 30.7 | 18.8 | 8 |
| Production Ex. 2 | WAR (B) | — | — | — | 0.1 | 5.2 | 34.6 | 5.9 | 36.6 | 6.2 | 0 |
| Example 5 | WAR (6) | APS/PEG-OMe/W = 2.5/0.5/24 | 10 | 15 | 6.5 | 24.3 | 16.1 | 16.3 | 21.6 | 21.5 | 163 |
| Example 6 | WAR (7) | APS/PEG-OMe/W = 2.5/0.5/32 | 10 | 15 | 6.7 | 30.0 | 12.6 | 13.8 | 18.4 | 19.7 | 340 |
| Example 7 | WAR (8) | APS/PEG-OMe/W = 2.5/0.5/40 | 10 | 15 | 9.6 | 32.4 | 11.6 | 12.7 | 17.6 | 18.8 | 417 |

TABLE 2-continued

| | Composition of treating solution (wt. %)) | Mixing time of treating solution (min.) | Irradiation time of UV (min.) | Surface water content (wt. %) | Total water content (wt. %) | Total water content before correction CRC (g/g) | Total water content before correction AAP (g/g) | Total water content after correction CRC (g/g) | Total water content after correction AAP (g/g) | SFC ($10^{-7} \cdot cm^3 \cdot s \cdot g^{-1}$) |
|---|---|---|---|---|---|---|---|---|---|---|
| Control 5 | WAR for com. (5) APS/PEG-OMe/W = 2.5/0.5/4 | 10 | 15 | 1.1 | 12.8 | 30.0 | 7.0 | 34.6 | 8.0 | 0 |
| Control 6 | WAR for com. (6) APS/PEG-OMe/W = 2.5/0.5/16 | 10 | 15 | 5.2 | 20.0 | 19.4 | 17.9 | 24.5 | 22.4 | 91 |

WAR: Water absorbent resin,
WAR for com.: Water absorbent resin for comparison
PEG-OMe: Polyethylene glycol monomethyl ether (a number average molecular weight of about 2,000)
APS: Ammonium persulfate
W: Pure water It is noted from the results shown in Table 1 that according to the method for the production of this invention, by irradiating the water absorbent resin composition with active energy rays, water and a water-soluble radical polymerization initiator with a surface water content of the water absorbent resin being controlled to a level of not lower than a predetermined value, the modification of the surface of the water absorbent resin particle can be effectively conducted, to produce a water absorbent resin having excellent water absorbent properties. Further, it is also noted from the results of Example 4 that by irradiating water absorbent resin with active energy rays while controlling the surface water content of the water absorbent resin to a level of not less than a prescribed value by adding relatively large amount of water thereto, the modification of surface of water absorbent resin particles can be efficiently carried out even in a short time and a water absorbent resin having excellent water absorbent properties can be produced.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an absorbent member comprising modified water absorbent resin, said absorbent member being suitable for use in absorbent articles, said method comprising the steps of:

a) providing an absorbent member; and b) providing modified water absorbent resin, said modified water absorbent resin being made by a method comprising:

(i) a mixing step comprising mixing water absorbent resin, water, and a heat-degradable radical polymerization initiator without addition of an ethylenically unsaturated monomer, to obtain a water absorbent resin composition, and (ii) an irradiating step comprising irradiating said water absorbent resin composition obtained in the mixing step with active energy rays, and wherein the amount of water mixed in said step (i) exceeds 20 parts by weight and is not more than 100 parts by weight based on 100 parts by weight of the water absorbent resin, and wherein the surface water content of said water absorbent resin in said water absorbent resin composition at least at any point of time in the irradiating step (ii) is controlled to a level of not lower than 3.0% according to the equation: (m)=(1)×((k)/100) wherein m is the surface water content in wt %, 1 is the weight ratio of the amount of water contained in a treating solution in wt % and k is the extraction ratio in wt %;

c) furnishing said absorbent member said water absorbent resin, which has been made by the method of step b).

2. The method according to claim 1, wherein said water-soluble radical polymerization initiator is at least one member selected from the group consisting of persulfates, hydrogen peroxide and water-soluble azo compounds.

3. The method according to claim 1, wherein the surface water content at the time of beginning said irradiating step is controlled to a level of not lower than 3.0% by weight.

4. The method according to claim 1, wherein the amount of said radical polymerization initiator in the mixing step is in the range of 0.01 to 20 parts by weight, based on 100 parts by weight of the water absorbent resin.

5. The method according to claim 1, wherein in the mixing step, said radical polymerization initiator is mixed in the form of an aqueous solution.

6. The method according to claim 1, wherein a mixing aid is added to the water absorbent resin simultaneously with carrying out the mixing step (i) or prior to the mixing step (i).

7. The method according to claim 1, wherein said water absorbent resin contains an acid group and has a neutralization ratio in the range of from 50 to 75 mol %.

8. The method according to claim 1, wherein said active energy rays are ultraviolet rays.

9. The method according to claim 1, wherein said water absorbent resin is a powdery water absorbent resin obtained by polymerizing a monomer containing an acrylic acid as a main component.

10. The method according to claim 1, wherein said water absorbent resin contains particles, 90% to 100% by weight of said particles having a particle diameter in the range of from 150 to 850 μm.

11. The method according to claim 1, wherein the absorbency of physiological saline against pressure of 4.83 kPa of the water absorbent resin after the modification is in the range of from 8 to 40 g/g.

12. The method according to claim 1, wherein the saline flow conductivity of the water absorbent resin after the modification is not less than $10 \times 10^{-7} \cdot cm^3 \cdot s \cdot g^{-1}$.

* * * * *

UNITED STATES PATENT AND TRADEMARK OFFICE
CERTIFICATE OF CORRECTION

PATENT NO.       : 7,745,507 B2
APPLICATION NO.  : 11/732589
DATED            : June 29, 2010
INVENTOR(S)      : Yoshiro Mitsukami et al.

It is certified that error appears in the above-identified patent and that said Letters Patent is hereby corrected as shown below:

Column 20
Line 12, delete "Sipemat" and insert -- Sipernat --.

Column 23
Line 43, delete "(σξ)" and insert -- (σζ) --.
Line 58, delete "(σξ)" and insert -- (σζ) --.
Line 60, delete "σξ" and insert -- σζ --.
Line 62, in the chemical formula, delete "σξ" and insert -- σζ --.

Signed and Sealed this
Eighteenth Day of January, 2011

David J. Kappos
*Director of the United States Patent and Trademark Office*